(12) United States Patent
Caron et al.

(10) Patent No.: US 9,149,230 B2
(45) Date of Patent: Oct. 6, 2015

(54) APPARATUS, SYSTEM AND METHODS FOR MEASURING A BLOOD PRESSURE GRADIENT

(71) Applicant: THREE RIVERS CARDIOVASCULAR SYSTEMS INC., Toronto (CA)

(72) Inventors: Eric Caron, Toronto (CA); Luc Bilodeau, Verdun (CA); Michel Paquette, Toronto (CA)

(73) Assignee: Three Rivers Cardiovascular Systems Inc., Toronto (CA)

( * ) Notice: Subject to any disclaimer, the term of this patent is extended or adjusted under 35 U.S.C. 154(b) by 0 days.

(21) Appl. No.: 14/354,624

(22) PCT Filed: Oct. 26, 2012

(86) PCT No.: PCT/IB2012/055893
§ 371 (c)(1),
(2) Date: Apr. 28, 2014

(87) PCT Pub. No.: WO2013/061281
PCT Pub. Date: May 2, 2013

(65) Prior Publication Data
US 2014/0249386 A1 Sep. 4, 2014

Related U.S. Application Data

(60) Provisional application No. 61/552,778, filed on Oct. 28, 2011, provisional application No. 61/552,787, filed on Oct. 28, 2011.

(51) Int. Cl.
*A61B 5/00* (2006.01)
*A61B 5/01* (2006.01)
(Continued)

(52) U.S. Cl.
CPC .............. *A61B 5/6855* (2013.01); *A61B 5/01* (2013.01); *A61B 5/026* (2013.01); *A61B 5/0215* (2013.01);
(Continued)

(58) Field of Classification Search
CPC .... A61B 5/0002; A61B 8/488; A61B 5/6855; A61B 5/02055; A61B 5/024; A61B 5/026; A61B 5/0295; A61B 5/0261; G06F 19/3418; G06F 19/3406

USPC .................................................. 600/300–301
See application file for complete search history.

(56) References Cited

U.S. PATENT DOCUMENTS 4,730,622 A * 3/1988 Cohen ........................... 600/480
4,735,212 A 4/1988 Cohen
(Continued)

FOREIGN PATENT DOCUMENTS

EP 1105181 A1 6/2001
WO 2011048509 A1 4/2011
(Continued)

OTHER PUBLICATIONS

Pinet et al.; "Ultra-miniature all-glass Fabry-Perot pressure sensor manufactured at the tip of a multimode optical fiber"; FISO Technologies Inc. ; Proceedings of SPIE, vol. 6770 (2007).
(Continued)

*Primary Examiner* — William Thomson
*Assistant Examiner* — Sebastian X Lukjan
(74) *Attorney, Agent, or Firm* — Miltons IPVp.l.

(57) ABSTRACT

An apparatus (100), control system (150) and methods are provided for directly measuring a pressure gradient, i.e. by real-time pressure measurements, with particular application for in situ measurement of transvalvular blood pressure gradients for the aortic valve and other heart valves, using minimally-invasive techniques. The apparatus takes the form of a multi-sensor assembly, e.g. enclosed within a micro-catheter or a steerable guidewire, and comprises a plurality of optical pressure sensors (10) is arranged along a length of the distal end portion (101), for measuring pressure simultaneously at each sensor location. For example, four MOMS optical pressure sensors (10), and optionally, a flow sensor (20), are incorporated into a distal end portion (101) having a diameter of 0.89 mm or less, and preferably 0.46 mm or less. Beneficially, all sensors are optically coupled, via respective optical fibers (11), to an optical coupler (112) at the proximal end of the multi-sensor apparatus, without requiring electrical connections.

27 Claims, 19 Drawing Sheets

(51) Int. Cl.
*A61B 5/026* (2006.01)
*A61B 5/0215* (2006.01)
*G01F 1/688* (2006.01)
*G01P 5/10* (2006.01)
*G01K 11/32* (2006.01)
*G01K 13/02* (2006.01)
*A61B 5/0205* (2006.01)
*A61B 8/08* (2006.01)
*G06F 19/00* (2011.01)
*A61B 5/0295* (2006.01)
*A61B 5/024* (2006.01)

(52) U.S. Cl.
CPC ........... *A61B 5/02055* (2013.01); *A61B 5/0261* (2013.01); *A61B 5/6852* (2013.01); *A61B 8/488* (2013.01); *G01F 1/6884* (2013.01); *G01K 11/32* (2013.01); *G01K 13/02* (2013.01); *G01P 5/10* (2013.01); *A61B 5/0002* (2013.01); *A61B 5/024* (2013.01); *A61B 5/0295* (2013.01); *G06F 19/3406* (2013.01); *G06F 19/3418* (2013.01)

(56) References Cited

U.S. PATENT DOCUMENTS

| | | | |
|---|---|---|---|
| 4,850,358 | A | 7/1989 | Millar |
| 4,953,553 | A | 9/1990 | Tremulis |
| 4,966,148 | A | 10/1990 | Millar |
| 5,018,529 | A | 5/1991 | Tenerz et al. |
| 5,125,058 | A | 6/1992 | Tenerz et al. |
| 5,226,423 | A | 7/1993 | Tenerz et al. |
| 5,392,117 | A | 2/1995 | Belleville et al. |
| 5,514,128 | A | 5/1996 | Hillsman et al. |
| 5,574,699 | A * | 11/1996 | Cuomo ................... 367/149 |
| 5,873,835 | A | 2/1999 | Hastings et al. |
| 6,112,598 | A | 9/2000 | Tenerz et al. |
| 6,167,763 | B1 | 1/2001 | Tenerz et al. |
| 6,254,550 | B1 * | 7/2001 | McNamara et al. .......... 600/585 |
| 6,336,906 | B1 | 1/2002 | Hammarstrom et al. |
| 6,343,514 | B1 | 2/2002 | Smith |
| 6,585,660 | B2 | 7/2003 | Dorando et al. |
| 6,615,667 | B2 | 9/2003 | Smith |
| 6,976,965 | B2 | 12/2005 | Corl et al. |
| 6,986,739 | B2 | 1/2006 | Warren et al. |
| 7,097,620 | B2 | 8/2006 | Corl et al. |
| 7,134,994 | B2 | 11/2006 | Alpert et al. |
| 7,274,956 | B2 | 9/2007 | Mott et al. |
| 7,329,223 | B1 | 2/2008 | Ainsworth et al. |
| 7,450,989 | B2 | 11/2008 | Svanerudh |
| 7,532,920 | B1 | 5/2009 | Ainsworth et al. |
| 7,689,071 | B2 | 3/2010 | Belleville et al. |
| 7,731,664 | B1 | 6/2010 | Millar |
| 7,783,338 | B2 | 8/2010 | Ainsworth et al. |
| 7,931,603 | B2 | 4/2011 | Von Malmborg et al. |
| 7,967,761 | B2 | 6/2011 | Smith |
| 7,967,762 | B2 | 6/2011 | Corl et al. |
| 2003/0095263 | A1 | 5/2003 | Varshneya et al. |
| 2003/0100824 | A1 | 5/2003 | Warren et al. |
| 2004/0075841 | A1 | 4/2004 | Van Neste et al. |
| 2004/0253365 | A1 | 12/2004 | Warren et al. |
| 2007/0038173 | A1 * | 2/2007 | Simpson ................... 604/22 |
| 2008/0249388 | A1 | 10/2008 | Kumhyr |
| 2010/0234698 | A1 | 9/2010 | Manstrom et al. |
| 2010/0241008 | A1 | 9/2010 | Belleville et al. |
| 2011/0023617 | A1 | 2/2011 | Yu et al. |
| 2011/0066047 | A1 | 3/2011 | Belleville et al. |
| 2011/0092784 | A1 | 4/2011 | Butler et al. |
| 2011/0234698 | A1 | 9/2011 | Sakata et al. |

FOREIGN PATENT DOCUMENTS

| | | |
|---|---|---|
| WO | 2011101813 A1 | 8/2011 |
| WO | 2012164481 A1 | 12/2012 |

OTHER PUBLICATIONS

Hamel et al.; "Temperature and pressure Fiber-Optic sensors applied to minimally invasive diagnostics and therapies"; FISO Technologies Inc.; Whitepaper/Publication; (2006).

Pinet, Eric; "Pressure measurement with fiber-optic sensors: Commerical technologies and applications"; FISO Technologies Inc.; 21st International Conference on Optical Fiber Sensors, edited by Wojtek J. Bock et al.; Proc. of SPIE vol. 7753 (May 17, 2011).

Pinet, Eric; "Disposable fiber-optic sensors for clinical environments"; SPIE 2007.

Tenerz, L; "A Fiberoptic Silicon Pressure Microsensor for Measurements in Coronary Arteries"; Radi Medical Systems; IEEE 1991.

Hamel et al."Pressure Fiber-Optic Sensors in Intra-aortic Balloon Pumping Therapy"; European Medical Device Manufacturer Editorial: Sensors and Transducers integrated in medical equipment or used in manufacturing process; FISO Technologies Inc.; Whitepaper/Publication; (2006).

FOP-F125 Pressure Sensor; FISO Technologies Inc.; Preliminary Datasheet dated 2008.

PressureWire Certus FFR Measurement System; Product information dated 2011 and 2009.

PressureWire Certus FFR Measurement System; Product Information; 2011.

Vaguine et al.; IEEE Transactions on Biomedical Engineering vol. BME-31, No. 1, pp. 168-172; Jan. 1984.

Silvestri et al.; Optical fiber measurement systems for medical applications; p. 205-225; Oct. 5, 2011.

* cited by examiner

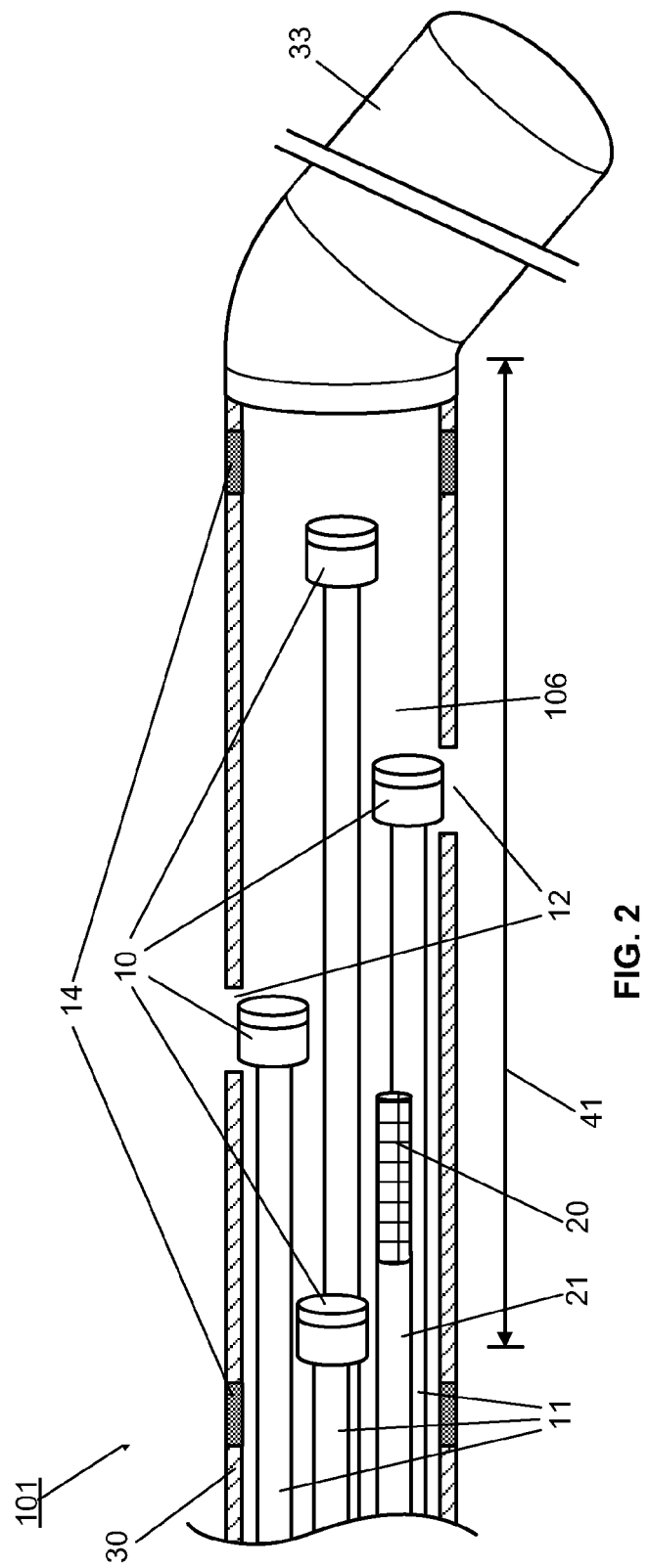

A-A CUT-THROUGH VIEW OF FIG. 1

B-B CUT-THROUGH VIEW OF FIG. 1

C-C CUT-THROUGH VIEW OF FIG. 1

D-D CUT-THROUGH VIEW OF FIG. 1

E-E CUT-THROUGH VIEW OF FIG. 1

F-F CUT-THROUGH VIEW OF FIG. 1

G-G CUT-THROUGH VIEW OF FIG. 1

A-A CUT-THROUGH VIEW OF FIG. 5

B-B CUT-THROUGH VIEW OF FIG. 5

C-C CUT-THROUGH VIEW OF FIG. 5

APPARATUS, SYSTEM AND METHODS FOR MEASURING A BLOOD PRESSURE GRADIENT

CROSS-REFERENCE TO RELATED APPLICATIONS

This application claims priority from U.S. provisional patent application No. 61/552,778 entitled "Apparatus, system and methods for measuring a blood pressure gradient", filed Oct. 28, 2011 and from U.S. provisional patent application No. 61/552,787 entitled "Fluid temperature and flow sensor apparatus and system for cardiovascular and other medical applications", filed Oct. 28, 2011, both of which are incorporated herein by reference, in their entirety.

TECHNICAL FIELD

This invention relates to an apparatus, system and methods for measuring fluid pressure gradients, and in particular, relates to measurement of blood pressure gradients and flow within the heart or blood vessels, including measurement of transvalvular blood pressure gradients.

BACKGROUND ART

In vertebrate animals, the heart is a hollow, muscular organ having four pumping chambers: the left and right atria and the left and right ventricles, each being provided with its own one-way valve. Thus, there are four heart valves: the mitral valve and the tricuspid valve, which are called atrio-ventricular valves, and the pulmonary valve and the aortic valve, which are called ventriculo-arterial valves. In one cycle of cardiac contraction, a valve opens to let blood flow from one side to the other, and then it closes to prevent backflow in the other direction. Thus, in the diastolic phase, the atrio-ventricular valves open to enable filling of the ventricles while the ventriculo-arterial valves remain closed. Conversely, in the systolic phase (ventricular contraction) of the cardiac cycle, the mitral and tricuspid valves close, while the pulmonary and aortic valves open to enable ejection of blood downstream of the ventricles.

Heart valve disease or dysfunction can, in severe cases, substantially restrict day to day activities and shorten the lives of patients. The primary procedure is valve repair or replacement surgery. In more than 20 percent of cardiac surgeries, heart valve disease represents the principal reason for a type of cardiac operation known as "open heart" surgery. These operations are associated with significant morbidity and mortality according to multiple risk factors related to age. New minimally-invasive procedures have been proposed to improve overall success. They involve inserting a valve made from animal tissue into the body using catheters and placing it inside the original diseased valve. However, both valve repair and replacement techniques remain particularly expensive and are associated with important risks for the patients.

It is therefore important to be able to quantify accurately the severity of valve disease, identify the right diagnosis and provide the proper treatments to patients. In addition, following a heart valve procedure, it is also fundamental to assess and monitor the physiologic performance of the new or repaired valve.

Heart valve pathologies may include a defect in closing or opening of a valve, or a combination of these two dysfunctions. Epidemiologically, a defect in opening of the aortic valve remains one of the most frequent anomalies. The three usual causes of aortic valve stenosis remain, in order of importance: calcified degeneration of the valve attributable to age, but certainly accentuated by hypertension; a congenital anomaly called bicuspid aortic valve, in which the valve possesses only two rather than three cusps (a cusp may also be referred to as a leaf or leaflet); and acute rheumatic fever (a particular bacterial infection at an early age, with subsequent excess scarring).

Diagnosis of aortic valve stenosis relies, first and foremost, on the appearance of symptoms in the patient, namely, breathlessness and chest pain on exertion, as well as loss of consciousness. Diagnosis is made through physical examination of the patient revealing a characteristic systolic murmur on auscultation, and a slower than normal rise of the pulse. Following that, transthoracic echography may confirm the clinical impression, e.g. by measuring an abnormal thickening of the layers of the heart valves, presence of calcifications, as well as restriction of the movement of the opening of the valve (*Braunwald's Heart Disease: A Textbook of Cardiovascular Medicine*, Authors: Peter Libby, Robert O. Bonow, Douglas L. Mann and Douglas P. Zipes, pages 267-268). The Doppler effect can be used to measure the velocity of blood traversing through the valve. This type of examination (two dimensional imaging and Doppler) allows for evaluation of the maximal velocity of the transvalvular blood flow, the aortic valve surface area and the surface area of the left ventricle outflow tract (LVOT). Accordingly, a severe aortic stenosis is defined by:

a) maximal flow velocity of >4.5 m/sec;
b) a mean transvalvular pressure gradient>50 mmHg;
c) a ratio of the surface of the LVOT/aortic valve×TVI (Time Velocity Interval)<0.25; or
d) an estimated valve surface area of <0.75 cm$^2$ (*Braunwald's Heart Disease: A Textbook of Cardiovascular Medicine*, Authors: Peter Libby, Robert O. Bonow, Douglas L. Mann and Douglas P. Zipes, page 269).

Even though echo-cardiography remains the most frequently used method for confirmation of diagnosis, it is limited by the echogenicity of the patient, valvular calcifications and sub-valvular calcifications, as well as the presence of concomitant mitral valve pathology. The results of echo-cardiography are also strongly operator-dependent. Consequently, it would be preferable to have a diagnostic method that relies on an in situ measurement of the transvalvular pressure gradient, made directly via cardiac catheterization into the interior of the heart in the region of the valve concerned, and surrounding regions.

In situ measurements of pressure or flow can be made within the human body, by minimally-invasive techniques, using a pressure sensing catheter or a special guidewire equipped with an integrated pressure sensor (see, for example, *Grossman's cardiac catheterization, angiography, and intervention*, Authors: Donald S. Bairn and William Grossman, pages 647-653).

Classically, this measurement of a transvalvular pressure difference, or pressure gradient, is made by two pressure sensing catheters positioned upstream and downstream, respectively, of the valve of interest, e.g. the aortic valve. To do this, the transeptal approach uses a Brockenbrough needle, and a Mullins type catheter to permit access, via the femoral vein, to the left atrium, by perforating the inter-atrial septum, then traversing the mitral valve, to place the tip of the catheter in the left ventricular cavity. A second catheter is introduced through the common femoral artery, to be positioned in the ascending aorta, just above the cusps of the aortic valve. Simultaneous measurements of the pressure upstream and downstream of the aortic valve can thus be obtained.

An alternative to this method involves placing a first arterial catheter through the aortic valve in the left ventricle and then introducing a second arterial catheter, and positioning it above the aortic valve in the ascending aorta. However, in this technique there is an exaggeration of the transvalvular pressure gradient since one of the catheters rests through the valve.

In another method, one can also simply measure the transvalvular gradient with only one arterial catheter, by a "pull back" method, i.e. inserting the catheter, crossing the valve into the ventricle and once the ventricular pressure measurement has been made, quickly withdrawing from the left ventricle into the ascending aorta, and subsequently measuring the aortic pressure. This last technique is clearly less reliable since, firstly, the measurements of the aortic and ventricular pressures are not simultaneous and secondly, the withdrawal of the catheter frequently involves a benign transitory cardiac arrhythmia, which distorts the pressure curves.

A variant of the latter approach was reported in an experimental study (*Feasibility of a Pressure Wire and Single Arterial Puncture for Assessing Aortic Valve Area in Patients with Aortic Stenosis*, J. H. Bae et al., J. Invasive Cardiol., 2006 August, 18(8), pp. 359-62). A pressure sensing wire, inserted through a guiding catheter, was used to measure pressure in the left ventricle using the pressure sensing wire, while simultaneously measuring pressure in the aorta using the guiding catheter. In practice, the technique is used infrequently. Firstly, it is not ideal to use different types of devices for comparing the two pressures. Also, in practice, the pressure sensing wire described is used for measuring pressures within small blood vessels, such as coronary arteries, and is therefore of small diameter and very flexible. It is therefore too limp and fragile for reliably positioning it for pressure measurements within the heart, where higher blood flows and significant turbulence in the flow tends to cause movement of the sensor at the end of the wire.

To calculate the cardiac flow, thermodilution by a Swan-Ganz catheter or the method of Fick are commonly used (*Grossman's cardiac catheterization, angiography, and intervention*, Authors: Donald S. Baim and William Grossman, pages 150-156).

Besides diagnosing a heart valve condition, measurements of a blood pressure gradient in blood vessels may be used to diagnose and treat patients with multi-site vessel disease. In order to quantify lesion severity in a diffusely affected vessel, pressure measurements are made at several locations along the vessel. This is currently done by withdrawing a pressure sensor equipped guidewire along a length of the vessel from a distal to a proximal position very slowly during a steady-state maximum induced hyperaemia. This diagnostic shows the location and severity of lesions but accuracy is compromised by the sequential nature of the data.

In view of limitations, such as limited accuracy, of the above-mentioned apparatus and techniques, there is a need for improved or alternative systems, apparatus and methods of operation for directly measuring and monitoring blood pressure gradient in real time, more accurately and reliably than is now possible, using minimally-invasive techniques.

A pressure sensing catheter is effectively a fluid-filled catheter: a pressure at the distal end, positioned in the region of interest, is measured by monitoring the fluid pressure in the catheter at the proximal end. A pressure sensing catheter for sensing pressure within the heart is typically 6 to 8 French in outer diameter (0.078" to 0.104"), in order to maintain enough rigidity and robustness. Typically, a pressure sensing guidewire equipped with an electrical pressure sensor can be made with a smaller diameter. This is advantageous for applications such as transvalvular pressure measurements or for measurements in small blood vessels such as coronary vessels.

One type of commercially available sensor equipped guidewire, PressureWire Certus from St. Jude Medical, uses a Micro-Electro-Mechanical-Systems (MEMS) device that includes a piezoresistor and diaphragm, e.g. as described in U.S. Pat. Nos. 5,343,514 and 6,615,667 to Smith (Radi Medical Systems AB) entitled "Combined flow, pressure and temperature sensor". Deformation of the diaphragm, caused by a pressure change, is read using resistance values. Other similar systems using MEMS technologies monitor the capacitance value between a fixed plate and the diaphragm to evaluate the deformation of the diaphragm due to pressure changes.

As explained above, available single pressure sensor guidewires can measure pressure at only one point at a time, and to measure a pressure gradient, the guidewire sensor must be moved through a region of interest, such as through a heart valve, or other vascular region, to measure pressure sequentially at several different points.

A problem with guidewires equipped with sensors based on electrical signals is that multiple, long electrical connections to each sensor must be provided. The length of a guidewire may be more than 1 meter. Use of microelectronics and long electrical wires, particularly when used in humid biological conditions, tends to cause reliability issues with measurement of small electrical signals, e.g. from parasitic capacitances, noise and electromagnetic interference (EMI), and limits the ability to integrate multiple electrical sensors within a guidewire to measure pressure gradient and flow. Furthermore, there may be significant risks involved with the use of microelectronics and electrical connections in vivo, particularly in the region of the heart, where electrical activity may disrupt normal heart function.

The electronic drift of MEMS sensors integrated into guidewires remains a limitation. For example, in one study, it was reported that measured pressures dropped >5 mmHg/hour, due to drift, therefore causing pressure gradient overestimation (*Coronary Pressure*, Authors: Nico Pijls and Bernard de Bruyne, pages 125-127).

Additionally, the guidewire is fabricated to provide the required flexibility and torque characteristics to enable the guidewire to be steered and positioned. Thus, the guidewire usually includes torque steering components comprising a central wire or mandrel, and external coil, e.g. a fine spiral metal coil, and a J-shaped tip (pre-shaped or manually shaped).

A guidewire used for cardiology may typically have a gauge of between 0.89 mm (0.035") and 0.25 mm (0.010") for introduction into small blood vessels. Note: catheter gauge may also be specified in French units: 1 French=0.333 mm diameter (0.013"). It will be appreciated that there is a limit to the number of electrical wires, sensors and steering components that can physically fit within the required diameter guidewire. Even if larger guidewires could be inserted, they would tend to interfere with normal operation of a heart valve and distort measurements, so it is desirable that the guidewire is as small gauge as possible. This presents a number of challenges in providing a guidewire with more than one electrical sensor.

In addition, MEMS sensors along with their long electrical connections significantly increase the complexity of manufacturing assembly processes of guidewires using electrical sensors, and therefore significantly increasing their manufacturing costs. Typically, guidewires for medical use are fabricated to be disposable (i.e. for single use only) and are significantly expensive.

To provide multi-sensor capability with a single electrical connection, U.S. Pat. No. 6,615,667 discloses a single combined flow, pressure and temperature MEMS sensor, but again, pressure can be measured at only one point.

To avoid the need for wired electrical connections entirely, optical pressure sensors are also known which are optically coupled to the control unit by optical fibers. However, another challenge for medical applications, as described above, is that to measure pressure gradients, pressure sensors are required having sufficient sensitivity to detect small pressure differences reliably within the region of interest. Some available optical sensors are either too large to allow for multiple sensors to be accommodated in a small gauge device, and/or they do not have sufficient sensitivity.

U.S. Pat. No. 4,735,212 to Cohen (Cordis Corporation) entitled "Multiple site fiber-optic pressure transducer" and U.S. Pat. No. 4,543,961 to Brown (Cordis Corporation) entitled "Data transmission system" discloses early designs for integrating several miniaturized pressure transducers or sensors arranged in a relatively large, i.e. 1.5 mm (0.060") single fiber device. These designs are quite complex and would appear to be a challenge to fabricate consistently. More significantly, the sensor elements will be sensitive to stresses when the fiber is bent or twisted, such that it would be difficult to discriminate fiber stresses from actual pressure readings. Thus, even if they could be manufactured with sufficiently small diameters, these and similar configurations would not be suitable for intravascular or intravalvular use which necessitate bending of the fiber in the region of the sensors.

Another known type of single point optical pressure sensor is a Micro-Opto-Mechanical Systems (MOMS) device that comprises a Fabry-Perot optical cavity where one of the two mirrors is a diaphragm. Low-coherence light is sent to the cavity via an optical fiber. Diaphragm motions are measured from spectral changes of the reflected light. Miniaturized pressure sensors of this type are described, for example, in U.S. Pat. No. 6,684,657 to Donlagic et al. (Fiso Technologies Inc.) entitled "Single Piece Fabry-Perot Optical Sensor and Method of Manufacturing the Same", and also in U.S. Pat. No. 7,689,071 to Belleville et al. (Opsens Inc.) entitled "Fiber-optic pressure sensor for catheter use". The use of this type of sensor for use in cardiovascular applications is relatively recent.

In summary, existing guidewire apparatus, using various types of sensors, are available for single point pressure measurements, for example, from St. Jude Medical and Volcano Corporation. However, apparatus is not currently known or available to cardiologists for directly measuring in situ blood pressure gradients simply and quickly, particularly transvalvular pressure gradients, where a catheter with a diameter of 0.89 mm (0.035") and preferably 0.46 mm (0.018") or less is needed to minimize disruption to normal heart valve activity and overestimation of transvalvular gradient. It would also be desirable to enable measurements for simultaneous determination of cardiac output and valvular area.

Thus, there is a need for improved or alternative systems, apparatus and methods for direct measurement and monitoring of blood pressure, pressure gradients and/or flow within the heart and the vascular system, and in particular, for measurement of transvalvular pressure gradients and flow velocity.

SUMMARY OF INVENTION

The present invention seeks to mitigate one or more disadvantages of the known systems, apparatus and methods, or at least provide an alternative.

Aspects of the invention thus provide an apparatus, system and methods for measuring a fluid pressure gradient, such as a blood pressure gradient, using a multi-sensor assembly, which may take the form of a micro-catheter or steerable guidewire, for example. Preferably, multiple optical microsensors allow for measuring pressure at multiple locations simultaneously and optionally, one or more other sensors may be provided for measuring flow velocity, or other parameters such as temperature.

Thus, a first aspect of the invention provides an apparatus for measuring a fluid pressure gradient comprising: a multi-sensor assembly extending from a proximal end to a distal end portion, the distal end portion comprising a sensor means comprising a plurality of optical sensors for measuring pressure at a plurality of locations along a length of the distal end portion; an optical coupling between each of the plurality of optical sensors and an optical input/output at the proximal end; a covering layer extending over the multi-sensor assembly and providing an aperture adjacent each optical sensor; and the distal end portion thereof having a diameter suitable for introduction intravascularly or intraluminally through a micro-catheter.

The optical sensors preferably comprise Micro-Opto-Mechanical Systems (MOMS) pressure sensors, and more preferably comprise Fabry-Pérot MOMS sensors.

The optical sensors are optically coupled to an optical input/output at a proximal end of the micro-catheter or guidewire via optical fibers, or other flexible light guides. The optical coupling preferably comprises a plurality of optical fibers, and each optical pressure sensor is optically coupled to the input/output by a respective one of the plurality of optical fibers. The sensor means may optionally comprise a flow sensor, which is preferably an optical flow sensor, but may also be an electrical flow sensor or other appropriate type of flow sensor.

When the flow sensor comprises an optical flow sensor, for example, an optical thermoconvection flow sensor, the optical coupling further comprises an optical fiber coupling the optical flow sensor to the optical input/output. Thus, the apparatus comprises sensor means comprising an arrangement of a plurality of optical sensors and a plurality of optical fibers, each fiber coupling at least one optical pressure sensor or an optical flow sensor to the optical input/output at the proximal end.

The flow sensor may comprise an electrical flow sensor and the multi-sensor assembly further comprises electrical connections coupling the electrical flow sensor to an electrical input/output at the proximal end. The flow sensor may comprise a resistive/ohmic thermoconvection flow sensor, or alternatively a Doppler effect flow sensor.

The covering layer may, for example, comprise polymer tubing in the form of a micro-catheter surrounding the sensor means and the plurality of optical fibers, the micro-catheter extending from the proximal end to a tip at the distal end, and the micro-catheter having an aperture in the distal end portion adjacent each sensor.

The covering layer or micro-catheter comprises, for example, a polymer tubing, which may be polyimide or PTFE, for example, or other suitable flexible, bio-compatible or hemo-compatible material, with appropriate mechanical properties. In some embodiments, the covering layer comprises a multilayer tubing. Preferably, the outside diameter of the polymer tubing surrounding at least said length of the distal end portion has a diameter of 0.89 mm (0.035") or less. More preferably, the diameter is 0.46 mm (0.018") or less. Thus, the outer layer, or covering, encloses and protects the multi-sensor assembly along the length of the optical fibers and comprises an aperture adjacent each pressure sensor, i.e. to allow contact of surrounding fluid with each sensor for pressure measurement. An outer protective jacket may also be provided around the proximal end portion.

Preferably, the dimensions of the components of the multi-sensor assembly provide for an apparatus wherein the distal end portion has an outside diameter of 0.89 mm (0.035") or less, and more preferably of 0.46 mm (0.018") or less.

Thus, in one embodiment, suitable for measurement of transvalvular pressure gradients, the apparatus comprises a plurality of sensors provided along a length of the distal end portion, for example, four or more optical pressure sensors arranged at intervals along a length of 4 cm to 7 cm of the distal end portion, near the distal tip. The overall length of the multi-sensor apparatus may be 1 m to 2 m, typically 1.5 m to 1.8 m.

In apparatus for medical applications, it is desirable that the multi-sensor assembly is enclosed within an envelope or outer/covering layer that extends along its length. A suitable flexible covering layer protects the optical components, while allowing the apparatus to be introduced intraluminally or intravascularly, and/or filled or flushed with fluid, such as saline solution.

In some embodiments, the apparatus further comprises torque steering components, e.g. a mandrel extending axially along the length of the multi-sensor assembly and an outer layer comprising a coil, i.e. a fine wire coil similar to that of a conventional guidewire. The latter may have an external diameter along the length of the distal end portion of <0.89 mm and preferably 0.46 mm or less, and optionally may comprise a J-tip. Thus, the multi-sensor apparatus takes the form of a steerable guidewire, with the coil acting as the covering layer, enclosing the sensors and their optical fiber connections to the input/output connector. The coil provides apertures near each sensor to allow for fluid contact during pressure measurements in a surrounding fluid.

The optical input/output means may comprise part of an optical connector at the proximal end for coupling the multi-sensor apparatus to a control system, i.e. to provide optical coupling for each optical sensor, and optionally the connector provides an electrical connection for an electrical sensor, if required. The input/output means may further provide for wireless connectivity with the control system.

In an embodiment of an apparatus for measuring a transvalvular or intra-arterial blood pressure gradient and flow velocity, the sensing means comprises a plurality of at least four optical pressure sensors and an optical flow sensor arranged along a length of the distal end portion matched to a dimensions of the transvalvular or intra-arterial region of interest; and each sensor is optically coupled to the input/output means at the proximal end by a respective individual optical fiber, each of the sensors and optical fibers having outside diameters such that they are accommodated within a catheter or guidewire having an outside diameter of <0.89 mm and preferably 0.46 mm or less.

In another embodiment of an apparatus for measuring a transvalvular or intra-arterial blood pressure gradient and flow velocity, the sensing means comprises a plurality of at least four optical pressure sensors and an electrical flow sensor, arranged along a length of the distal end portion matched to a dimension of the transvalvular or intra-arterial region of interest; each optical pressure sensor is optically coupled to the input/output means at the proximal end by a respective individual optical fiber, and the electrical flow sensor is provided with a pair of electrical connections; each of the sensors, the optical fibers and the electrical connections have outside diameters such that they are accommodated within a catheter or guidewire having an outside diameter of <0.89 mm and preferably 0.46 mm or less.

Thus, for example, a small gauge multi-sensor apparatus for intravascular use may comprise, e.g., two, four or perhaps eight pressure sensors arranged at the distal end for sensing pressure at a plurality of locations simultaneously, together with a flow sensor for measuring flow velocity.

In one embodiment, a small gauge multi-sensor wire comprises four optical pressure sensors arranged along a length, e.g. 4 cm to 7 cm, at the distal end of the wire, which allows for placement of two sensors on each side of a heart valve, to allow direct measurement of the transvalvular pressure gradient, with minimal disruption to the valve function.

In some embodiments, a plurality of optical pressure sensors may be combined with an electrical flow sensor, e.g. a conventional ohmic thermoconvection flow sensor may be used, thus requiring only one pair of electrical wires. Optionally, additional types of sensors, such as a temperature sensor may be included.

The multi-sensor wire may be provided in a micro-catheter and have a straight tip to allow it to pass easily through a heart valve, and so that it may be introduced through a conventional support catheter or guide catheter, which may already be in place for other cardiac procedures. Optionally, the multi-sensor wire may comprise torque steering elements, such as a conventional mandrel and coil arrangement, and optionally, a J-shaped tip, to allow the multi-sensor wire to be introduced, torqued and steered as a conventional guidewire.

Yet another aspect of the invention provides a control system for a multi-sensor wire apparatus, wherein the control system comprises a light source means and detection means for coupling to each of the optical sensors. The control system optionally comprises electrical connections for an electrical sensor.

The system may further comprise processing means, comprising hardware and/or software, for processing optical data indicative of pressure gradient values and/or optical or electrical data indicative of flow velocity values, and deriving pressure and flow data therefrom.

In an embodiment, a system for measuring an intravascular or transvalvular blood pressure gradient further comprises processing means, e.g. hardware and/or software, for graphically displaying data representing a blood pressure gradient and/or flow velocity data for one or more time intervals, and during one or more cardiac cycles.

Another aspect of the invention provides a multi-sensor-assembly for an apparatus for measuring a fluid pressure gradient, the multi-sensor assembly extending from a proximal end to a distal end portion, and comprising: a sensor arrangement comprising a plurality of optical sensors for measuring pressure, the sensors being positioned along a length of the distal end portion for simultaneously measuring pressure at a corresponding plurality of locations along said length; a plurality of optical fibers, each fiber being coupled at a proximal end to an optical input/output at the proximal end of the assembly and each fiber being optically coupled at a proximal end to an individual one of the plurality of optical sensors; and the distal end portion having a diameter suitable for introduction intraluminally through a micro-catheter.

A further aspect of the invention provides a method for measuring a transvalvular blood pressure gradient comprising: providing a multi-sensor wire; introducing and advancing the distal end portion of the multi-sensor wire into the heart and through the valve to be monitored; positioning the pressure sensing means to place one or more pressure sensors at locations upstream of the valve and other sensors at locations downstream of the valve to be monitored; and activating the sensors and obtaining data simultaneously from each sensor to obtain a blood pressure gradient during one or more time intervals.

Also provided is a method for measuring an intra-arterial or other intra-vascular blood pressure gradient comprising: providing a multi-sensor wire; introducing and advancing the distal end portion of the multi-sensor wire into the arterial or other vascular region to be monitored; positioning the pressure sensing means to place the pressure sensors at locations along the length of the region to be monitored; and, activating the sensors and obtaining data simultaneously from each sensor to obtain a blood pressure gradient during one or more time intervals.

The method may further comprise simultaneously obtaining flow velocity data, and may comprise gathering blood pressure gradient and flow velocity data over one or more cardiac cycles, and graphically displaying the data from one or more of the sensors.

Thus, a small gauge, integrated multi-sensor apparatus or "multi-sensor wire", e.g. in the form of a micro-catheter or steerable guidewire, is provided that allows for direct measurement of a blood pressure differential or a blood pressure gradient, i.e. the comparison of real-time, direct blood pressure measurements at several locations simultaneously, within heart ventricles, arteries and/or veins during a minimally-invasive intravascular intervention. In particular, a multi-sensor wire having a diameter of 0.89 mm or less, and preferably 0.46 mm or less, provides for transvalvular pressure gradient measurements with minimal or negligible disruption of the heart valve function.

In addition, the multi-sensor wire allows for measurement of data to provide indirect measurement of a cardiac blood output and, as a consequence, estimation of the cardiac obstruction surface, i.e. the valve area.

A multi-sensor wire according to embodiments of the invention therefore provides for novel methods for directly and precisely measuring a transvalvular pressure gradient in situ for any one of the four heart valves. Beneficially, these methods provide for improvements to existing cardiovascular measurement techniques, i.e. the comparison of real-time direct blood pressure measurements at several locations simultaneously, e.g. upstream, across and downstream of the heart valve, for each of the four heart valves, during minimally-invasive (percutaneous intravascular) cardiovascular procedures.

Such methods provide measurements that enable cardiologists to more accurately quantify parameters or data indicative of the severity of valve disease, such as structural valve stenosis, and then promptly identify the diagnosis and provide the appropriate treatments to patients. In addition, following a heart valve procedure, such as valvuloplasty or valve replacement, clinicians can assess or monitor the physiologic performance of the new or repaired heart valve.

An apparatus comprising a multi-sensor assembly, a multi-sensor wire or guidewire, a system and methods according to embodiments of the invention may also be used for directly measuring and monitoring a blood pressure gradient within blood vessels, in real-time, using minimally-invasive techniques.

It will also be appreciated that apparatus, systems and methods using the multi-sensor assembly have particular applications for the cardiovascular system; a similar multi-sensor wire system may also have applications in other systems of the body, i.e. for directly measuring a fluid pressure gradient or flow in other biological fluids, for both human and animal subjects, during a minimally-invasive procedure and/or for evaluating prosthetic medical devices.

Thus, apparatus, systems and methods are provided that mitigate problems with known methods and apparatus for measuring pressure gradients, and in particular provide for direct measurement of intravascular or transvalvular pressure gradients and flow.

The foregoing and other objects, features, aspects and advantages of the present invention will become more apparent from the following detailed description, taken in conjunction with the accompanying drawings, of embodiments of the invention, which description is by way of example only.

BRIEF DESCRIPTION OF THE DRAWINGS

In the drawings, identical or corresponding elements in the different Figures have the same reference numeral.

FIG. 2 illustrates schematically an enlarged longitudinal cross-sectional view showing details of the distal end portion of the multi-sensor wire illustrated in FIG. 1;

DETAILED DESCRIPTION OF THE EMBODIMENTS

Figure 1:
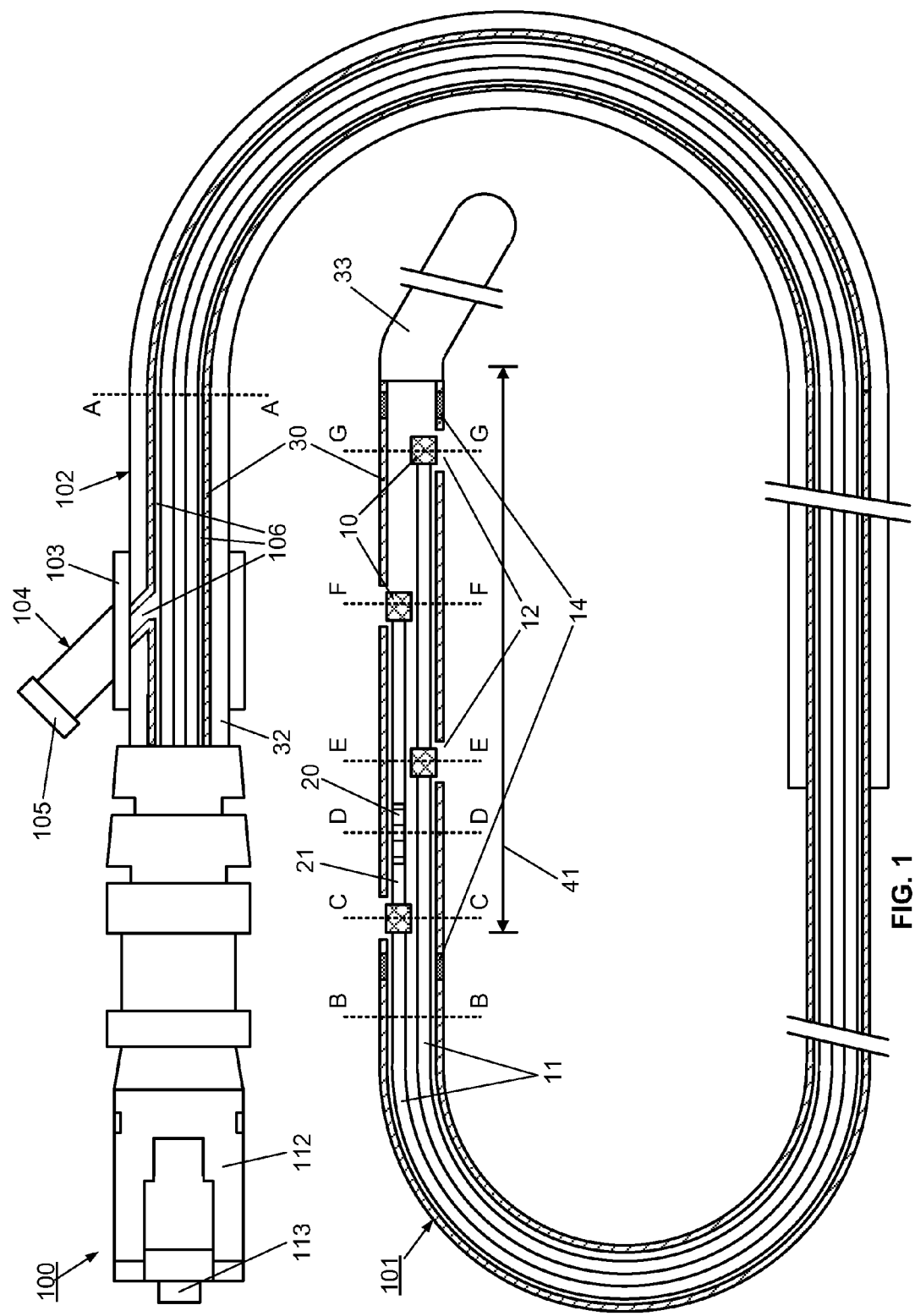
FIG. 1 illustrates schematically a longitudinal cross-sectional view of an apparatus comprising a multi-sensor assembly comprising a plurality of sensors according to a first embodiment of the present invention.
Figure 3A:
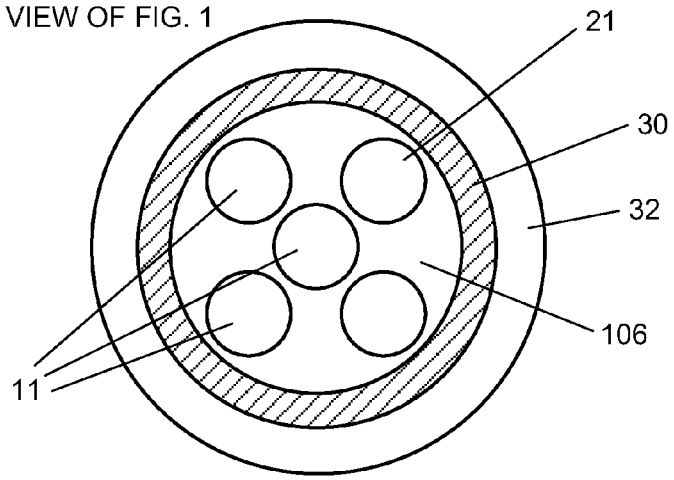
FIGS. 3A, 3B, 3C, 3D, 3E, 3F and 3G show enlarged axial cross-sectional views of the multi-sensor wire illustrated in FIGS. 1 and 2 taken through planes A-A, B-B, C-C, D-D, E-E, F-F and G-G respectively.
Figure 3B:
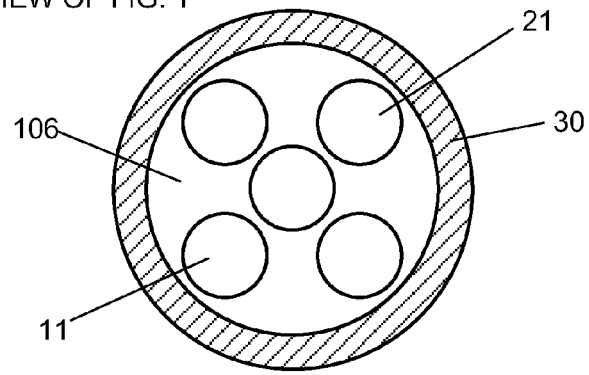
Figure 3C:
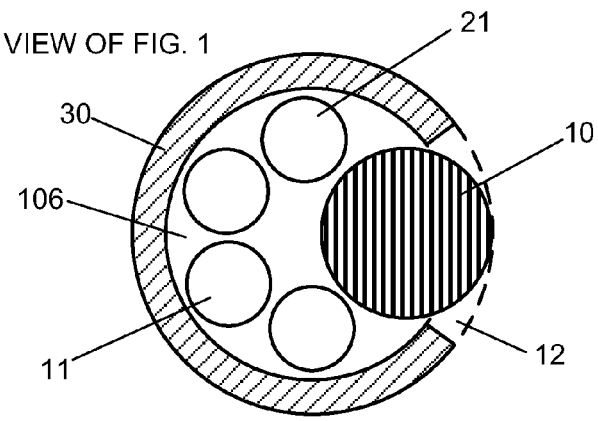
Figure 3D:
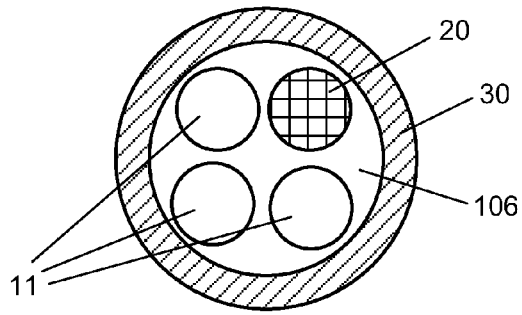
Figure 3E:
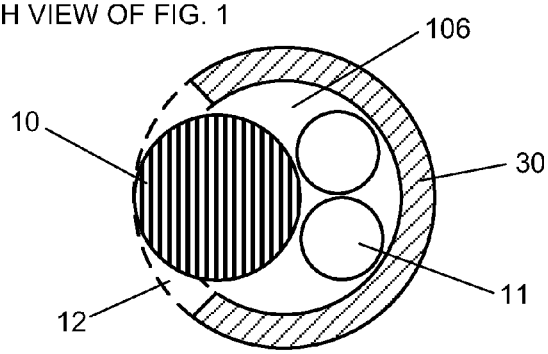
Figure 3F:
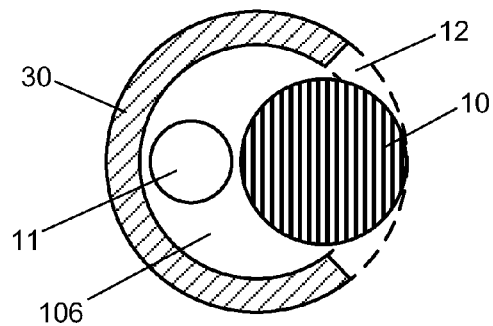
Figure 3G:
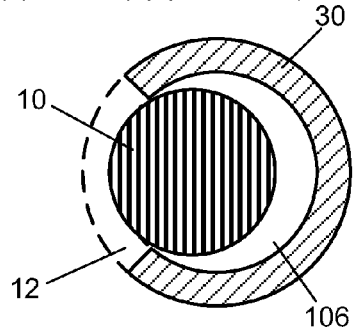

FIG. 1 illustrates a longitudinal cross-sectional view of an apparatus 100 according to an embodiment of the invention, in the form of a multi-sensor wire, for measuring blood pressure, pressure gradients, and flow velocity, showing the internal structure and components. The multi-sensor wire 100 has a suitable length and diameter for intravascular use, e.g. by introduction into the subject through a narrow gauge support catheter using a minimally-invasive procedure, as will be described in detail below. Near the tip 33, a distal end portion 101 of the a multi-sensor assembly comprises pressure and flow sensing means, which, in this embodiment, comprises an arrangement of a plurality of four optical pressure sensors 10 and an optical flow sensor 20. Each sensor is coupled via a respective individual optical fiber 11 to an optical input/output connector 112 at the proximal end 102, for coupling of the multi-sensor wire 100 to a control system (see FIG. 4). An outer layer or covering layer 30 is provided, comprising a single layer or multilayer tubing, that forms a covering or cladding for the multi-sensor assembly. In this embodiment, the layer 30 comprises a micro-catheter (e.g. a flexible polymer tubing) having a lumen 106 that surrounds the bundle of optical fibers 11 and extends to the rounded tip 33 at the distal end. The tip 33 is beneficially a soft flexible tip, as illustrated schematically, to facilitate insertion. At the proximal end 102 of the multi-sensor wire, a thicker protective jacket or sleeve 32 is also provided around layer 30. In the distal end portion, apertures 12 are provided in the tubing 30, adjacent each of the sensors 10. Radio-opaque markers 14 are also provided at several locations along the length of the distal portion 101 to assist in location of the sensors during measurements. Although the structure of the multi-sensor assembly is shown in cross-section along its length from the connector 112 to the distal tip 33, for simplicity, the internal structure of the connector 112 is not shown. It will be appreciated that the optical fibers 11 extend through the connector to optical inputs/outputs 113 of the connector, as is conventional.

As shown in FIG. 1, the multi-sensor wire 100 optionally comprises, at the proximal end, a hub 103 providing a Y connector to a side arm 104 with a port 105 which gives access to the lumen, i.e. the cavity or space, 106. Such a port is conventionally provided in a catheter or guidewire for flushing or filling the lumen with a fluid. The lumen 106 extends the around optical fibers 11 along the length of the polymer tubing 30 to the apertures 12, near each of the sensors 10, at the distal end of the multi-sensor wire. In use, the port 105 in the side arm provides the capability for flushing and filling the lumen 106 with fluid, e.g. normal saline solution, which assists in avoiding or removing any air bubbles, particularly those which may become trapped in the region of the sensors 10 near apertures 12, where bubbles may interfere with pressure measurements in the surrounding fluid.

FIG. 2 shows an enlarged longitudinal cross-sectional view of the distal end portion 101 of the multi-sensor wire 100 illustrated in FIG. 1. As illustrated, the multi-sensor wire 100 is capable of measuring blood pressure simultaneously at several points, in this case four points, using the four optic fiber-based pressure sensors 10 arranged along the length 41 of the distal end portion of the multi-sensor wire. For example, as shown, the sensors are arranged at equal intervals along a length of the distal end portion 101, which length is determined by the dimension of the heart or vascular region to be monitored. The multi-sensor wire 100 should preferably also be capable of measuring blood flow velocity since quantification of blood flow restriction is related to pressure difference and the blood flow velocity. It therefore includes an integral fiber-optic flow sensor 20 at a suitable position in the distal end portion 101 to measure the blood flow velocity.

FIGS. 3A, 3B, 3C, 3D, 3E, 3F and 3G show enlarged axial cross-sectional views of the multi-sensor wire 100 taken through planes A-A, B-B, C-C, D-D, E-E, F-F and G-G respectively, of FIG. 1, illustrating the location of the optical fibers 11, pressure sensors 10 and fiber-optic flow sensor 20 within the lumen 106 of polymer tubing 30. The polymer tubing 30 is typically a flexible tubing comprising one or more layers of polymer materials, such as polyimide or polytetrafluoroethylene (PTFE), or other suitable bio-compatible or hemo-compatible materials having the desired mechanical properties, and which allows the multi-sensor wire to be introduced and slide easily through a support or guide catheter. The radio-opaque markers 14 at the distal end allow the operator to locate the position of the sensors of multi-sensor wire 100 within vascular regions or within the heart using a conventional medical imaging system, such as a fluoroscope. Apertures 12 in the polymer tubing 30 allow sensors 10 and 20 to be exposed for pressure and flow measurements in the surrounding fluid, e.g. intravascular blood.

As illustrated schematically, each sensor 10 may be slightly larger in diameter than the optical fiber to which it is coupled. However, each of the optical pressure sensors 10 is a micro-sensor, preferably based on MOMS technologies, and more preferably they comprise a Fabry-Perot optical cavity, where one of the two mirrors is a diaphragm. Low-coherence light is sent to the cavity from the controller through the input/output connector 112 via the optical fiber 11. Diaphragm motions, due to pressure changes, are measured from spectral changes detected in the reflected light received back at the detector. Such sensors are described, for example, in U.S. Pat. Nos. 7,684,657 and 7,689,071.

Optical pressure sensors of this type, which may be optically coupled to a control system, e.g. via optical fibers or other flexible light guides, are substantially immune to humid conditions and to electromagnetic parasitic interferences and noise involved with long electric wires needed for electrical connections integrated within guidewires. Moreover, optical pressure sensors 10 can be manufactured with smaller dimensions, e.g., with an outside diameter of 250 µm or less, compared to MEMS sensors. Each optical pressure sensor requires coupling via a single optical fiber only rather than multiple wires required for MEMS sensors. Optical sensors are not susceptible to electronic drift that has been reported for some MEMS sensors. Therefore, these optical pressure sensors allow the integration of an assembly of multiple pressure sensors 10, within multi-sensor wires 100 having an outside diameter of 0.89 mm (0.035 inches) or less, and preferably, an outside diameter at the distal end of 0.46 mm (0.018 inches) or less.

As illustrated in FIG. 1, the flow sensor 20 also comprises an optical sensor, which advantageously comprises a novel optically coupled thermoconvection flow sensor, of a type which is described in more detail in the above referenced copending U.S. provisional patent application No. 61/552,787. Preferably, this micro-flow sensor preferably has a diameter similar to that of the optical fiber 11, i.e. 125 μm, to which it is coupled. Other suitable micro flow sensors may alternatively be used, e.g. a flow sensor either based on Doppler effect or on temperature sensitive resistors.

Thus, in an exemplary embodiment, the outside diameter of the multi-sensor wire 100 would be 0.53 mm (0.021 inches) across the sections B-B and C-C and 0.46 mm (0.018 inches) across the sections D-D, E-E and F-F (see FIG. 2 and FIGS. 3A to 3F). That is, the multi-sensor wire has to accommodate all five fibers 11 and 21 at cross-section B-B, but narrows slightly towards cross-section F-F where only one fiber and sensor extends. The measurement range of the pressure sensors 10 would be typically from −300 mmHg to +300 mmHg with an accuracy of +/−2 mmHg. The outside diameter of the optical fibers 11 and the pressure sensors 10 would be 0.125 mm (0.005 inches) and 0.260 mm (0.010 inches) respectively. As illustrated in FIG. 1, the pressure sensors 10 are typically located within a distance 41 of 4 to 7 centimeters (1.57 to 2.76 inches) from the tip 33 at the distal end of the multi-sensor wire 100.

In this embodiment, each pressure sensor 10 is optically coupled to an individual optical fiber 11, e.g. by adhesive bonding or other suitable bonding method. If necessary, a length of protective tubing, e.g. polyimide, may be provided around the optical sensor and a short length, e.g. a few mm, at the end of the optical fiber, to protect the bonded region and/or to provide mechanical reinforcement. Using a suitable manual or automatic alignment and adhesive bond, the bundle of individual fibers are aligned so that the sensors are arranged to provide the required spacing between each sensor. The total outside diameter of the pressure sensors 10 protected by the tubing would be about 0.30 mm (0.012 inches). A multi-sensor wire 100 would typically be provided with a rounded distal tip 33, which may be a soft flexible J-tip. The distance from the distal tip 33 of the multi-sensor wire 100 to the distal end of the jacket 32 would typically be about 1.6 m (63 inches).

Figure 4:
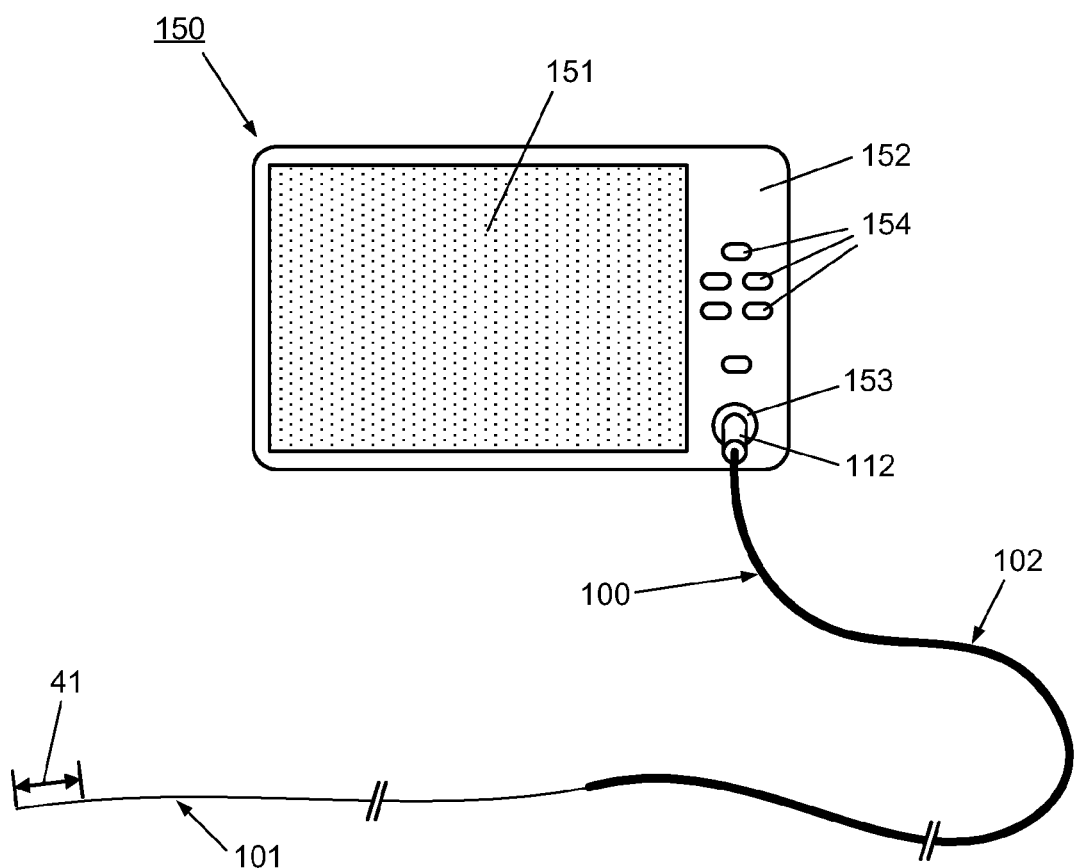
FIG. 4 illustrates schematically a system according to the first embodiment, comprising a multi-sensor wire coupled to a control system including a user interface.

As illustrated in FIG. 4, a multi-sensor wire system comprises the multi-sensor wire apparatus 100 and a system controller 150. The system controller 150 has a user interface front panel 152 and a graphical user interface 151 for displaying simultaneously, in real-time, charts showing the measurement data from the pressure sensors 10 at each location and from the fiber-optic flow sensor 20. The user interface includes controls 154 on the front panel 152 and/or as part of a touch screen 151. The multi-sensor wire 100 is attached to the system user interface 150 via the multi-sensor wire input/output connector 112 and the user interface input/output port 153.

The control system 150 includes a processor, with appropriate hardware and software for controlling the system and obtaining data indicative of pressure, flow and any other measured parameters from the sensors 10 and 20, and displaying or storing data in a desired format. It also includes a light source, from which light is sent to each optical pressure sensor 10 via its respective fiber 11, and a detection system for detecting changes in the light reflected back from the Fabry-Pérot sensors, which are indicative of pressure values. Similarly, light is sent down the respective fiber 21 to the flow sensor 20, and changes in the light received back at the detector are indicative of thermal changes dependent on flow velocity. If required, the controller 150 may include a separate higher intensity light source and detector for the optical flow sensor 20. If other electrical sensors or peripherals are used, the controller includes the appropriate electrical connections and electronics. The control system 150 may be a stand-alone unit, an optical control unit run from a PC, or part of a system integrated with other equipment used for cardiology procedures.

Methods for measurement and monitoring of transvalvular pressure gradients and flow for each heart valve, and for assessing or monitoring other blood vessels, will be described in detail in the following sections.

However, the use of the optical multi-sensor wire 100 in the form of a micro-catheter will first be described very briefly, so as to introduce a second embodiment in which the multi-sensor wire takes the form of a guidewire.

In summary, in use of the optical multi-sensor wire 100 in the form of a micro-catheter, for measurement of intravascular or transvalvular blood pressure gradients and flow, a cardiologist would first introduce a guide/support catheter to allow the optical multi-sensor wire to be quickly introduced into the region of interest. A guide catheter may already be in place for other cardiac procedures. If not, conventionally, this would involve first introducing a conventional guidewire, which can be torqued using established techniques, for other intravascular or cardiac procedures. Such a guidewire typically includes a J tip and has suitable flexibility and torque characteristics to allow it to be steered and guided to position the type in the region of interest, e.g. near the heart valve or stenosed region. The support/guide catheter is then introduced over the guidewire. The guidewire is then withdrawn, to allow subsequent introduction of the optical multi-sensor wire through the support catheter, and into the region of interest for pressure gradient and flow measurements. The radio-opaque markers on the multi-sensor wire or micro catheter allow for monitoring of the location of the multi-sensor wire and its sensors, while it is positioned in the region of interest, e.g. in the blood vessels or heart.

Once the array of sensors is positioned appropriately, and the multi-sensor wire is coupled to the control system, the sensors are activated to gather pressure and/or flow velocity data simultaneously from each sensor, for example, during one or more time intervals in a cardiac cycle, or over several cycles. Alternatively, while the sensors are activated, a pressure gradient data may be obtained simply and quickly from one position, and then sensor array may be moved to a different position for another measurement to explore the region of interest, while providing instantaneous pressure gradient and cardiac flow information. In some situations, it may be desirable to activate the sensors before positioning the multi-sensor wire to assist in finding the region of interest, e.g. a region of maximum restriction.

If a guide/support catheter is not already in place for other procedures, it is desirable to have a self-guiding multi-sensor wire.

Figure 5:
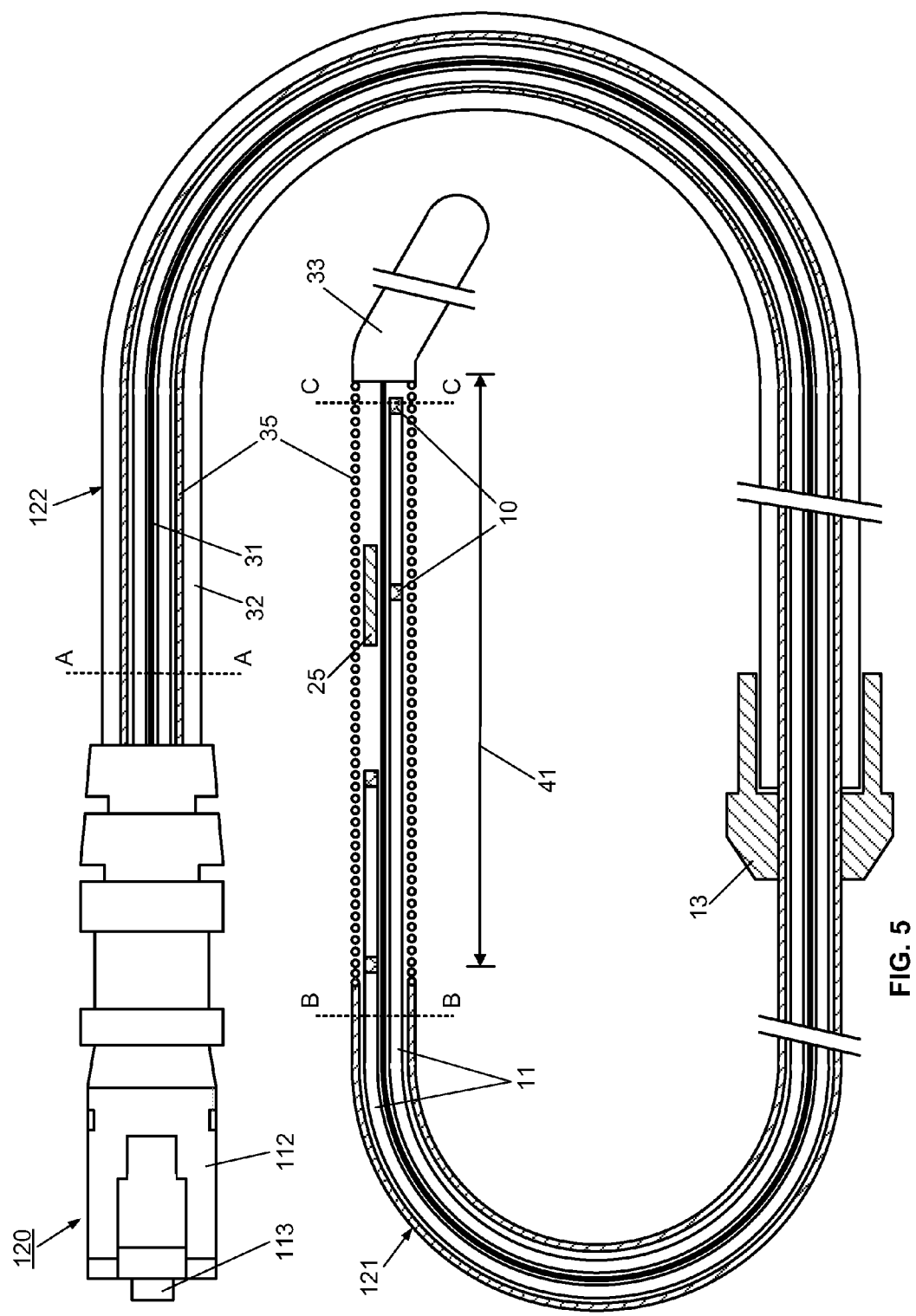
FIG. 5 illustrates schematically a longitudinal cross-sectional view of an apparatus comprising a multi-sensor wire assembly according to a second embodiment of the present invention, with integrated elements for guiding (i.e. torquing and steering) the multi-sensor wire.
Figure 6:
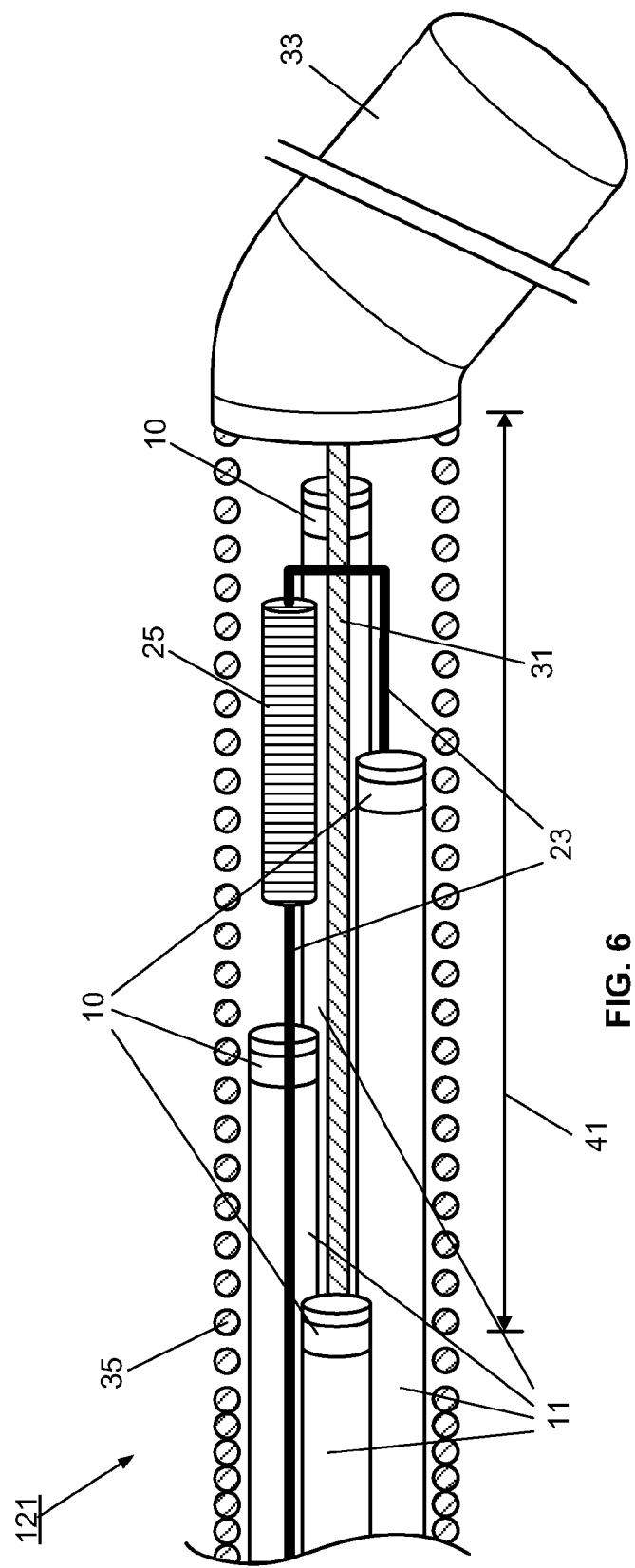
FIG. 6 illustrates schematically an enlarged longitudinal cross-sectional view of the distal end portion of the multi-sensor wire illustrated in FIG. 5.

Thus, a multi-sensor wire 120, according to a second embodiment of the present invention, is illustrated in FIGS. 5, 6 and 7, and takes the form of a guidewire, comprising integrated torque steering elements for guiding the multi-sensor wire, i.e. a mandrel, coil and J tip, similar to those used in a conventional guidewire. Referring to FIG. 5, all components that are similar to those of the multi-sensor wire 100 shown in FIGS. 1 to 4 are shown with the same reference numerals.

Thus, the multi-sensor wire 120 of the second embodiment differs from that of the first embodiment in comprising a central wire or mandrel 31, and a coiled outer layer 35, i.e. instead of the polymer tubing 30 of sensor wire 100, the outer layer is provided by a fine wire coil 35 made of metal alloy. A protective jacket 32 is provided on the proximal end. The coil 35, along with the mandrel 31, provides the steerable and torquable characteristics of the multi-sensor wire 120 so that is capable of being shaped or flexed to traverse vascular regions in the same manner as a conventional guidewire. The mandrel, coil and the J-shape distal tip 33 allows for the multi-sensor wire to be steerable using a conventional torque device 13 mounted on the proximal shaft.

Figure 7A:
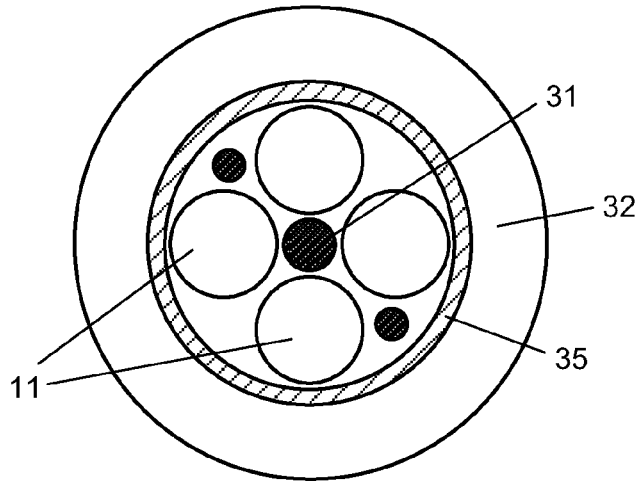
FIGS. 7A, 7B and 7C show enlarged axial cross-sectional views of the multi-sensor wire illustrated in FIG. 6 taken through planes A-A, B-B and C-C respectively.
Figure 7B:
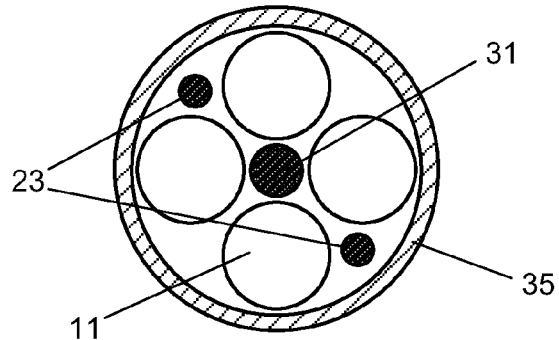
Figure 7C:
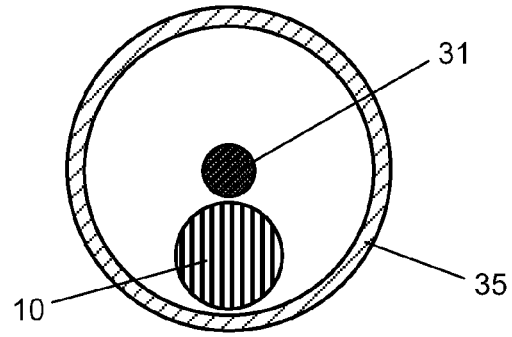

As shown in the enlarged longitudinal cross-sectional view in FIG. 6, at the distal end 121, the multi-sensor wire 120 comprises four optical pressure sensors 10 similar to those of the embodiments described above. Instead of an optical flow sensor, it integrates a flow sensor 25 in the form of a temperature sensitive resistor, i.e. a resistive thermoconvection sensor, or thermistor such as used in a Swann-Ganz catheter. For an electrical flow sensor of this type, a pair of electric wires 23 is provided within the coil 35 to connect the blood flow sensor 25 to the system user interface 150 via the multi-sensor wire connector 112. FIGS. 7A, 7B and 7C are enlarged axial cross-sectional views of the multi-sensor wire 120, taken at planes A-A, B-B and C-C respectively, illustrating the location of the optical fibers 11, mandrel 31, electrical wires 23 and pressure sensors 10 within the coil 35.

The multi-sensor wire 120 preferably has an outside diameter similar to that of the multi-sensor wire 100, i.e. an outside diameter of 0.89 mm or less and preferably 0.46 mm or less near the distal end.

Since the multi-sensor wire 120 is steerable, it can be introduced quickly for pressure gradient and flow measurements, without the need for first introducing a guide catheter. Measurement of pressure gradients may be made as the guidewire is advanced.

In a multi-sensor wire 130 according to another embodiment (not illustrated), instead of an all optical sensor embodiment described with reference to FIGS. 1 to 4, the optical flow sensor 20 may instead comprise a conventional resistive thermoconvection sensor 25, similar to that used in the second embodiment, which is coupled to an electrical connector of the control system by a pair of electrical wires 23 instead of optical fiber 21.

In yet another embodiment (not illustrated), an apparatus may be provided similar to that shown in FIG. 5, but using an optical flow sensor. This provides an all-optical multi-sensor wire implementation, and eliminates the need for an electrical connection.

While several embodiments are described and illustrated, by way of example, comprising four optical micro-pressure sensors and an optical flow sensor, it will be appreciated that other embodiments may be provided with different numbers and types of pressure and flow sensors. However, at least two pressure sensors are needed for measuring a pressure differential, and preferably, four or more pressure sensors are provided for measuring pressure gradients, e.g. two on each side of a heart valve or vascular region of interest. The spacing of the sensors along the distal portion of the multi-sensor wire may be selected to position the sensors at the suitable locations, but typically for cardiac applications, may be positioned for measuring a gradient along a length of about 4 cm to 7 cm, e.g. with four equally spaced sensors. For simultaneous measurement of flow at least one flow sensor is also required. Advantageously, optical pressure sensors eliminate the need for multiple long electrical connections and associated reliability issues, electromagnetic noise and interference issues. Radio-opaque markers may be provided on the sensors or at intervals along the multi-sensor wire as appropriate, but alternatively other suitable markers may be provided for use with other imaging modalities. If required, a port is provided for filling or flushing the lumen of the apparatus, e.g. a hub with a side arm port shown in FIG. 1, other conventional arrangement.

While it may be desirable to provide a greater number of sensors, e.g. eight or more, the number will be limited by the maximum permissible diameter of the multi-sensor wire, and the size of the sensors and optical fibers, and may be dependent on other factors such as required flexibility or stiffness of the multi-sensor wire. While Fabry-Perot MOMS pressure sensors are described, in alternative embodiments, other suitable miniature optical pressure sensors may be used. Optionally, other sensors, such as a temperature sensor, or a combined flow and temperature sensor may be provided.

If the multi-sensor wire does not include an integral flow sensor, the cardiac flow velocity may alternatively be measured conventionally by a separate Swan-Ganz catheter, by Doppler echography, by a Doppler effect flow sensor, or by the method of Fick.

Although a single optical connector 112 is shown for the input/output for each of the five of optical fibers 11, in other embodiments, an alternative connector or coupling arrangement may be provided. The multi-sensor wire connector 112 and the user interface port 153 may comprise several individual optic fiber connectors, instead of a single multi-fiber connector. In yet other embodiments, multiple sensors 10 and 20 may be coupled, via a multiport optical coupler at some point along the multi-sensor wire, to a single fiber, with multiplexing of signals from multiple sensors. The connector 112 may optionally include circuitry allowing wireless communication of control and data signals between the multi-sensor wire 100 and the system controller 150 and user interface 151. Optionally one or more electric connectors for peripheral devices, or for additional or alternative electrical sensors, may be provided.

It will also be appreciated that for medical or veterinary applications, the multi-sensor wire should be fabricated from suitable biocompatible materials, and provided in a suitable sterile packaged form. Typically the multi-sensor wire assembly is provided for single use, and is disposable. Thus, cost and environmental considerations may be important in selecting appropriate components and materials.

Figure 8:
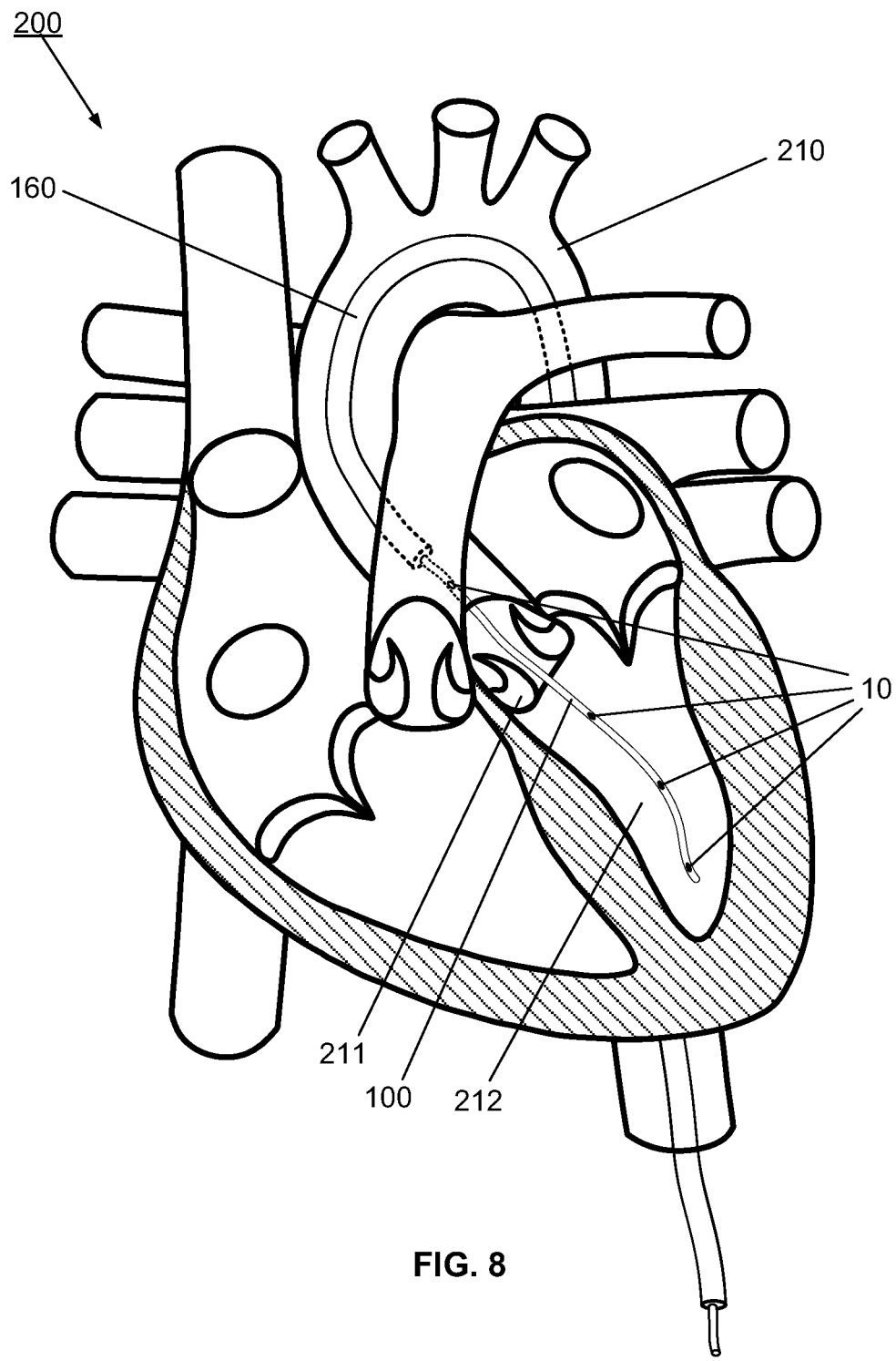
FIG. 8 shows a schematic of a human heart illustrating positioning of the multi-sensor wire of FIG. 1 during a method, according to a first embodiment, for measuring the blood pressure gradient across the aortic heart valve.

Measurement of Transvalvular Pressure Gradient Across the Aortic, Mitral, Tricuspid and Pulmonary Valves of the Heart A method, according to a first embodiment of the present invention, for measuring and monitoring the blood pressure gradient across the aortic valve 211, i.e. the aortic transvalvular pressure gradient, in a human heart 200 using a multi-sensor wire 100 according an embodiment, such as described with reference to FIGS. 1 to 4, is described below with reference to FIG. 8. A conventional guidewire is first inserted into a peripheral artery, such as the femoral or carotid, using known techniques, and advanced through the ascending aorta 210. A support catheter 160 is then slid over the guidewire. The operator then advances and positions the support catheter 160 in proximity to the aortic valve 211, using visualization devices such as radio-opaque markers on its distal end. The operator then replaces the guidewire by the multi-sensor wire 100 in the lumen of the support catheter 160. The operator advances and positions the distal end of the multi-sensor wire 100 into the left ventricle 212 using visualization devices such as radio-opaque markers 14 on its distal end. Once the multi-sensor wire 100 is properly positioned, the system measures the transvalvular pressure gradient of the aortic valve 211. As illustrated schematically in FIG. 8, three pressure sensors 10 are positioned in the left ventricle 212 and one pressure sensor is positioned in the aorta 160 just downstream of the aortic valve 211, to allow simultaneous measurements of pressure at four locations upstream and downstream of the valve. A series of measurements may be taken during several cardiac cycles. Although not illustrated in FIG. 8, a flow sensor 20 may also be provided for simultaneous flow measurements. Measurements results may be displayed graphically, e.g. as a chart on the graphical user interface 151 of the system controller 150 (see FIG. 4) showing the pressure gradient and flow. The control system may provide for multiple measurements to be averaged over several cycles, and/or may provide for cycle-to-cycle variations to be visualized. If appropriate, the multi-sensor wire may be alternatively positioned, e.g. to make measurements simultaneously at four different locations, for example with two pressure sensors positioned each side, i.e. upstream and downstream respectively of the aortic valve 213. Thus, the operator can quickly and easily obtain transvalvular pressure gradient measurements. Measurements may be made, for example, before and after valve replacement or valve repair procedures.

Figure 9:
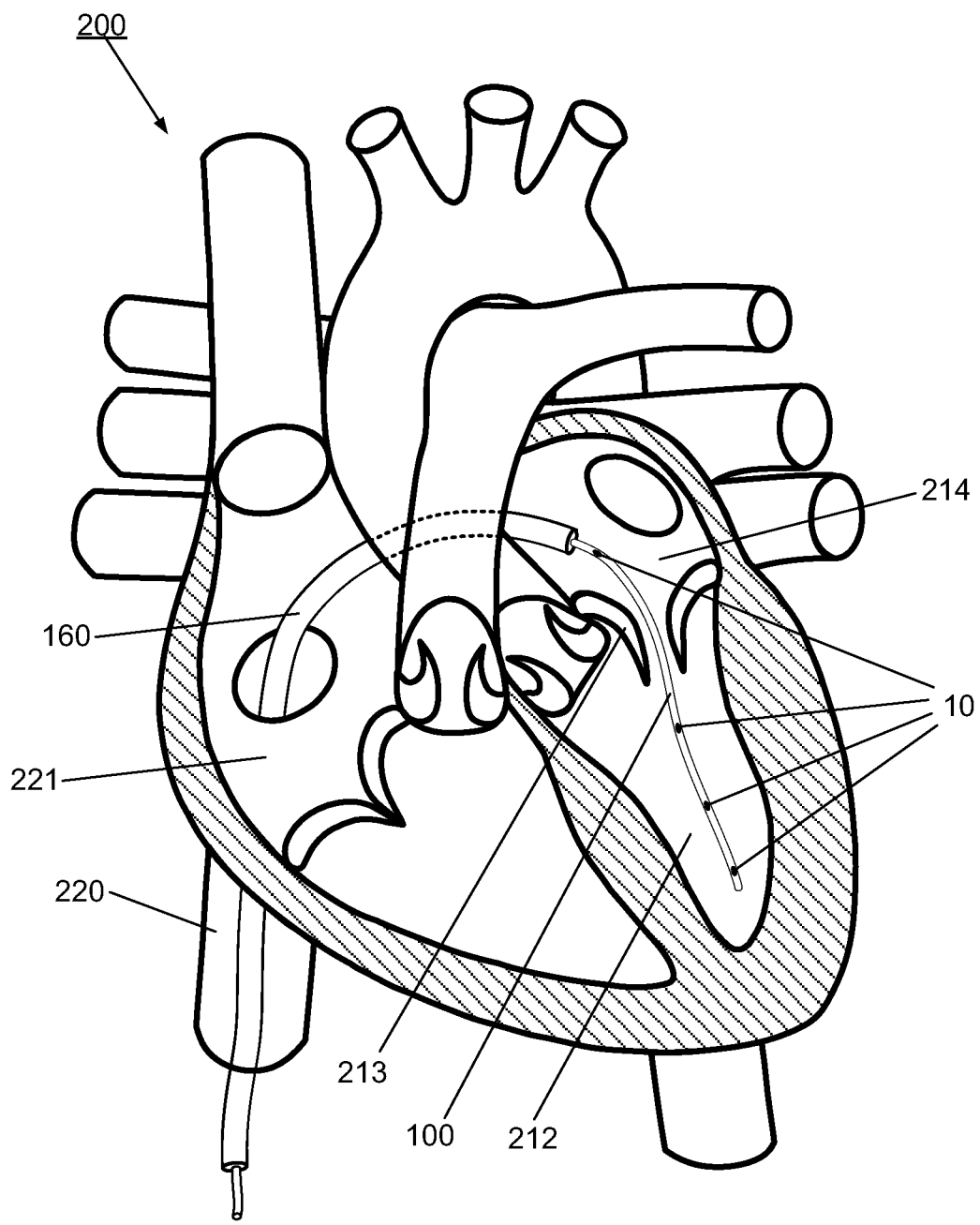
FIGS. 9, 10 and 11 show corresponding schematics of a human heart illustrating positioning of the multi-sensor wire during methods, according to other embodiments, for measuring the blood pressure gradient across the mitral, tricuspid, and pulmonary heart valves respectively.

A method, according to a second embodiment, to measure and monitor the blood pressure gradient across the mitral valve 213, i.e. the mitral transvalvular pressure gradient, in a human heart 200 is described below and illustrated by FIG. 9. A guidewire is first inserted into a peripheral large vein, such as the inferior vena cava 220, using known techniques, and advanced through the ascending vein 220 to the right atrium 221. The support catheter 160 is then slid over the guidewire. The operator then advances the support catheter 160 to the right atrium 221 and then crosses the septum to position the support catheter 160 in the left atrium 214 near the mitral valve 213, using known techniques. The operator then replaces the guidewire by a multi-sensor wire 100 in the lumen of the support catheter 160. The operator advances and positions the distal end of the multi-sensor wire 100 into the left ventricle 212, using visualization devices such as radio-opaque markers 14 on its distal end. Once the multi-sensor wire 100 is properly positioned, the system measures and displays the transvalvular pressure gradient of the mitral valve 213.

Figure 10:
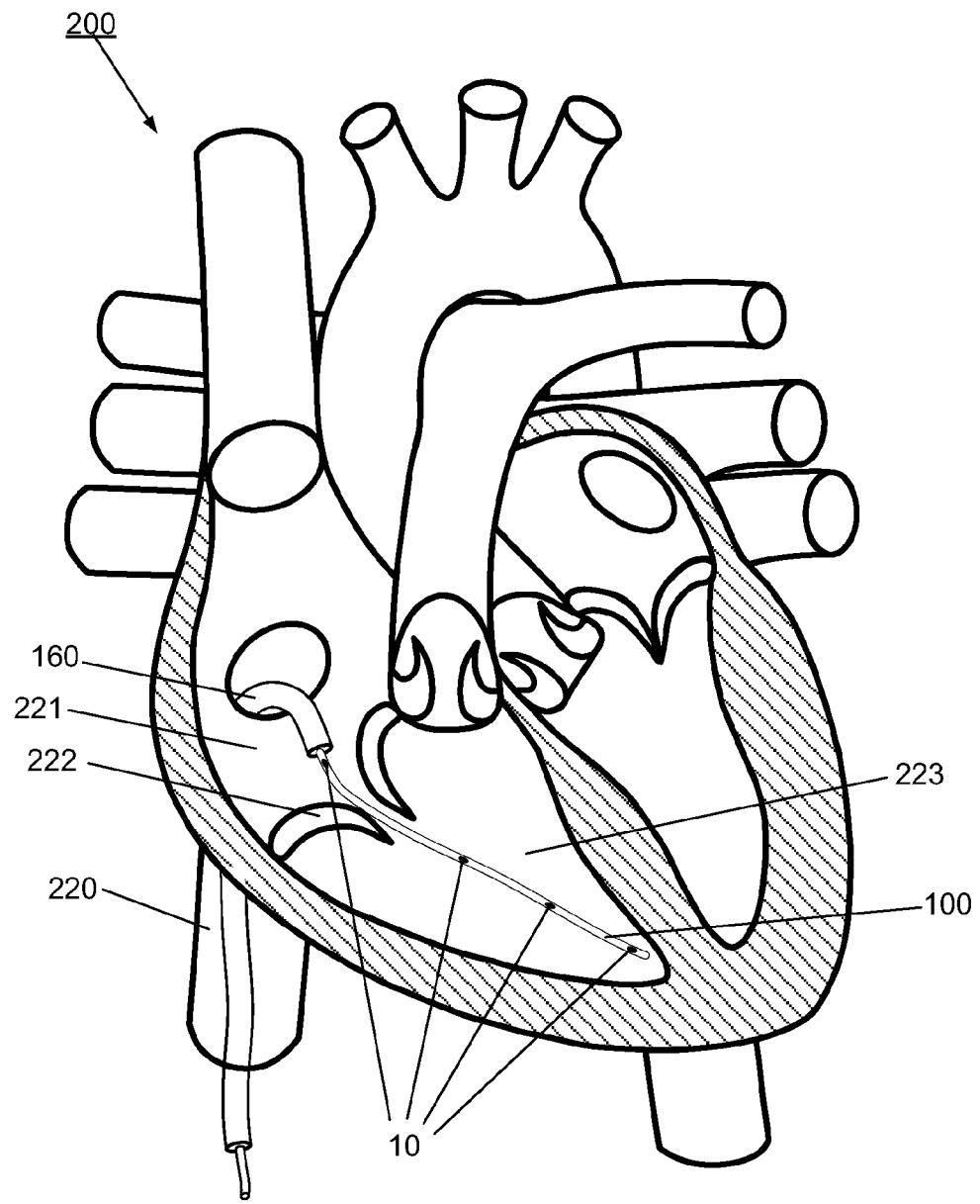

A method, according to a third embodiment, to measure and monitor the blood pressure gradient across the tricuspid valve 222, i.e. the tricuspid transvalvular pressure gradient, in a human heart 200, is described below and illustrated by FIG. 10. A guidewire is first inserted into a peripheral large vein, such as the inferior vena cava 220, using known techniques, and advanced through the ascending vein 220 to the right atrium 221. The support catheter 160 is then slid over the guidewire. The operator then advances and positions the support catheter 160 in proximity to the tricuspid valve 222, using visualization devices such as radio-opaque markers on its distal end. The operator then replaces the guidewire by a multi-sensor wire 100 in the lumen of the support catheter 160. The operator advances and positions the distal end of the multi-sensor wire 100 into the right ventricle 223 using visualization devices such as radio-opaque markers 14 on its distal end. Once the multi-sensor wire 100 is properly positioned, the system measures and displays the transvalvular pressure gradient of the tricuspid valve 222.

Figure 11:
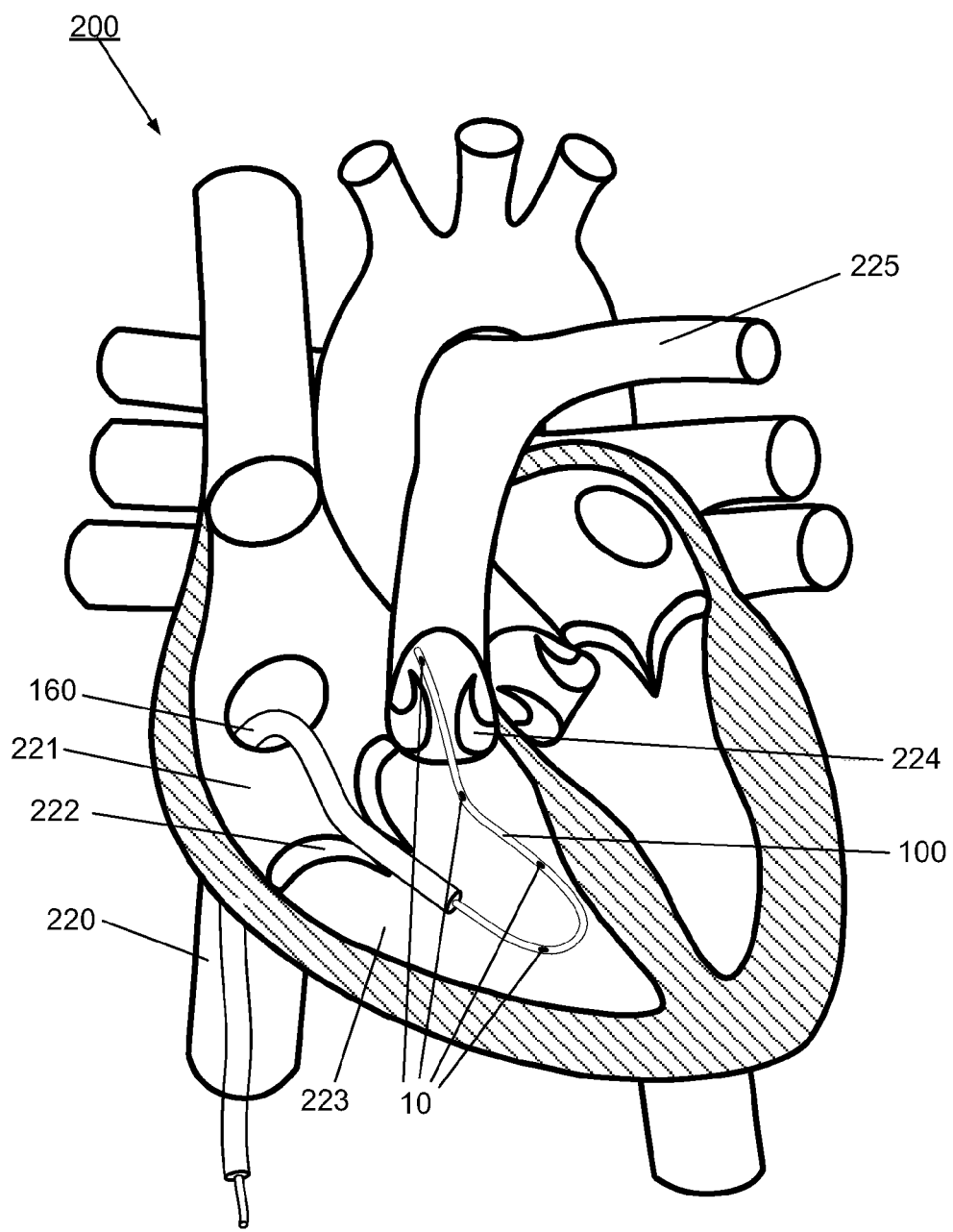

Similarly, in a fourth embodiment, a method to measure and monitor the blood pressure gradient across the pulmonary valve 224 (i.e. the pulmonary transvalvular pressure gradient) in a human heart 200 is described below and illustrated by FIG. 11. The operator advances and positions the distal end of the multi-sensor wire 100 into the right ventricle 223 using visualization devices such as radio-opaque markers 14 on its distal end as described above. The operator then further advances the support catheter 160 in proximity to the pulmonary valve 224. The operator then further advances and positions the distal end of the multi-sensor wire 100 into the pulmonary artery 225. Once the multi-sensor wire 100 is properly positioned, the system measures and displays the transvalvular pressure gradient of the pulmonary valve 224.

The function of the heart is to move de-oxygenated blood from the veins to the lungs and oxygenated blood from the lungs to the body via the arteries. The right side of the heart collects de-oxygenated blood in the right atrium 221 from large peripheral veins, such as, the inferior vena cavae 220. From the right atrium 221 the blood moves through the tricuspid valve 222 into the right ventricle 223. The right ventricle 223 pumps the de-oxygenated blood into the lungs via the pulmonary artery 225. Meanwhile, the left side of the heart collects oxygenated blood from the lungs into the left atrium 214. From the left atrium 214 the blood moves through the bicuspid valve 213 into the left ventricle 212. The left ventricle 212 then pumps the oxygenated blood out to the body through the aorta 210.

Figure 12:
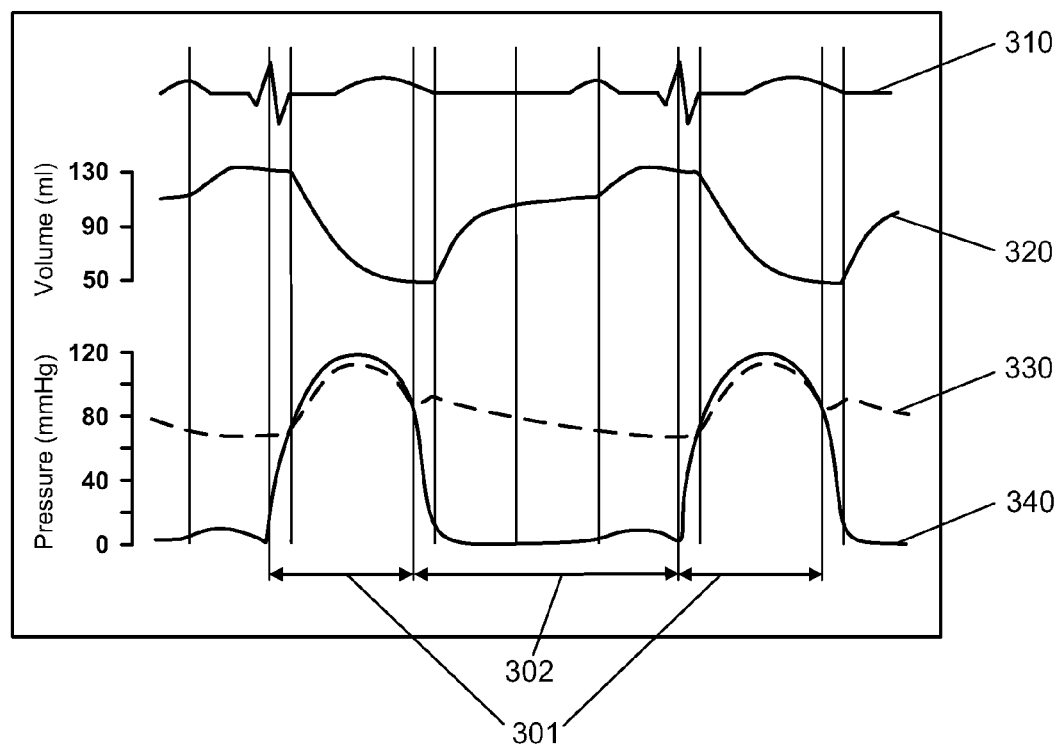
FIG. 12 shows a chart, known as a Wiggers diagram, showing typical cardiac blood flow and pressure curves during a heart cycle for a healthy heart.

Throughout the cardiac cycle, blood pressure increases and decreases into the aortic root 210 and left ventricle 212, for example, as illustrated by the pressure curves 330 and 340, respectively, in FIG. 12, which shows curves typical of a healthy heart. The cardiac cycle is coordinated by a series of electrical impulses 310 that are produced by specialized heart cells. The ventricular systole 301 is the period of time when the heart muscles (myocardium) of the right 223 and left ventricles 212 almost simultaneously contract to send the blood through the circulatory system, abruptly decreasing the volume of blood within the ventricles 320. The ventricular diastole 302 is the period of time when the ventricles 320 relax after contraction in preparation for refilling with circulating blood. During ventricular diastole 302, the pressure in the left ventricle 340 drops to a minimum value and the volume of blood within the ventricle increases 320.

Figure 13A:
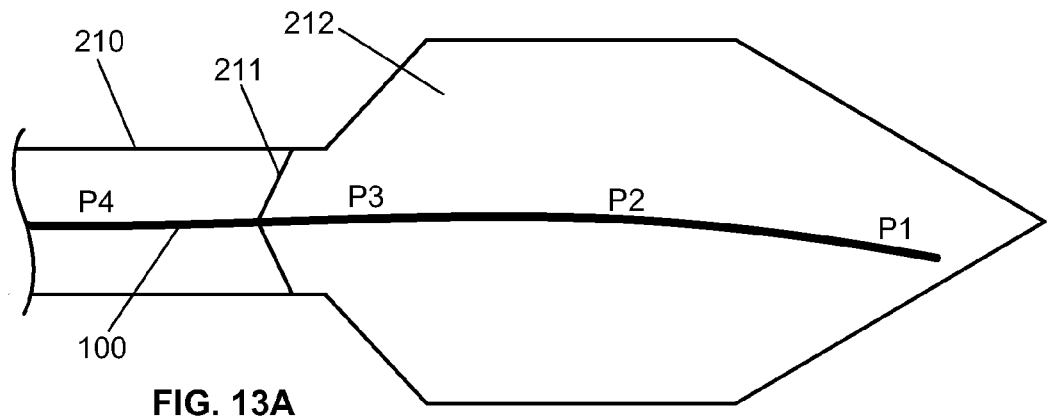
FIGS. 13A, 13B and 13C show simplified schematics representing the aortic heart valve and left ventricle during measurement of a transvalvular pressure gradient through the aortic valve in a healthy heart, as the heart valve opens.
Figure 13B:
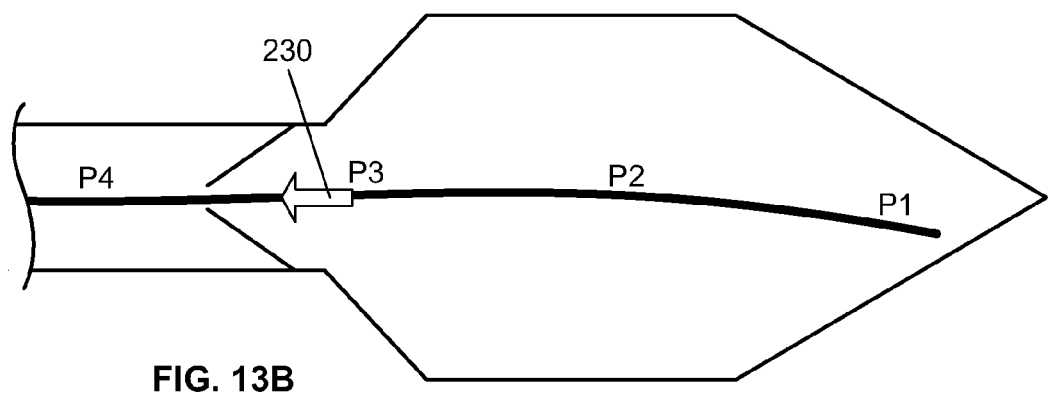
Figure 13C:
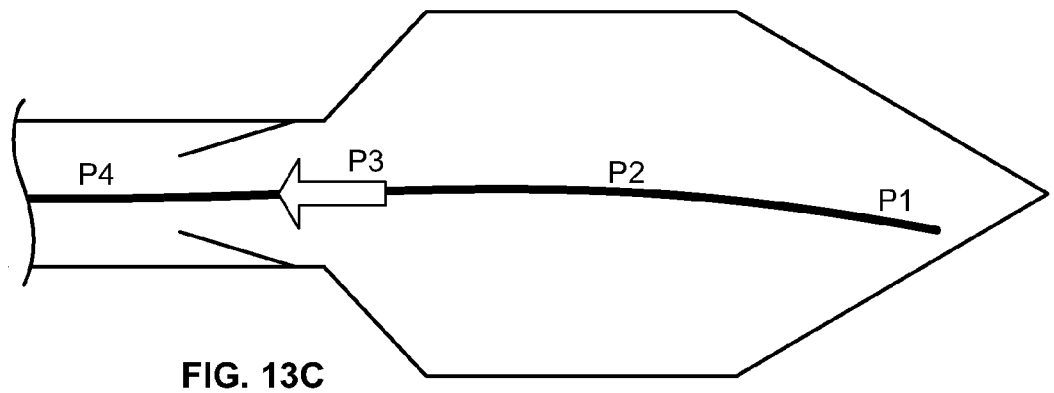
Figure 14A:
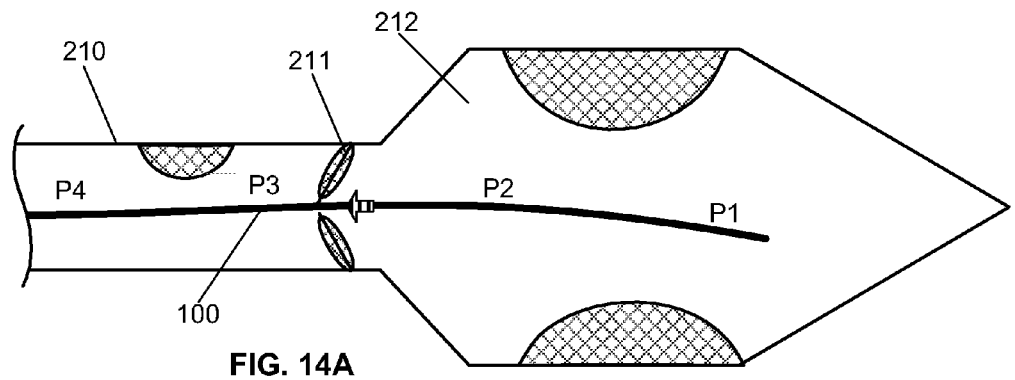
FIGS. 14A, 14B and 14C show similar simplified schematics representing the aortic heart valve and left ventricle, in which shaded areas represent stenoses, during measurement of a transvalvular pressure gradient through the aortic valve using a multi-sensor wire according to an embodiment of the invention.
Figure 14B:
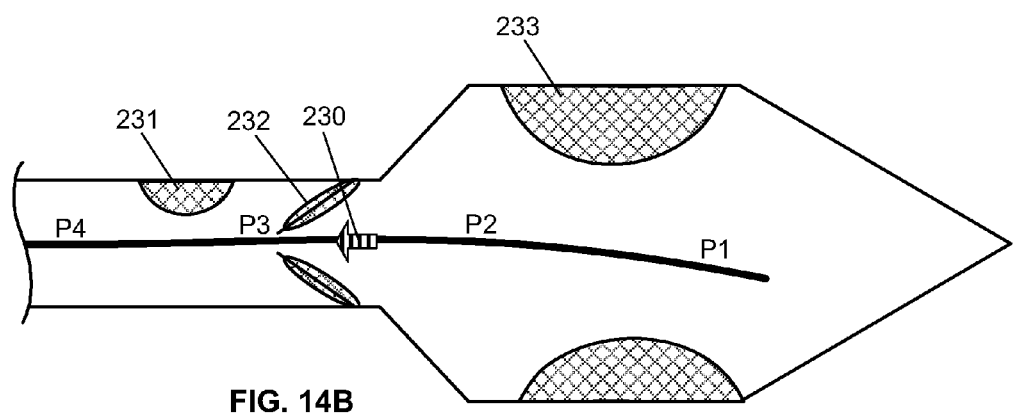
Figure 14C:
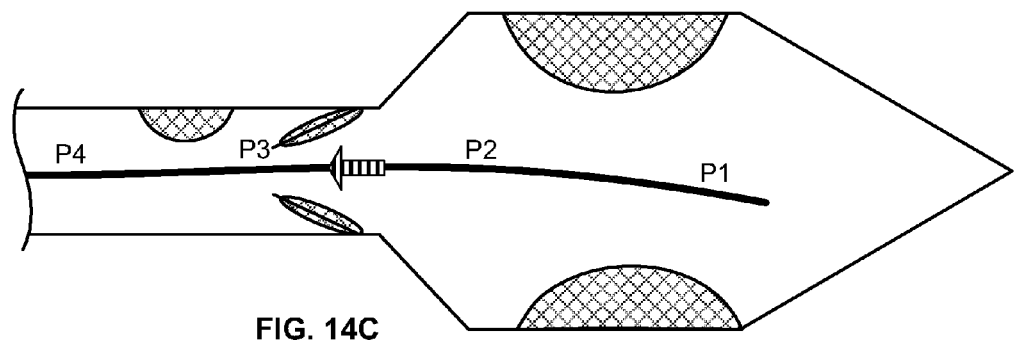

FIGS. 13 and 14 are simplified schematics of the aortic heart valve 211 and left ventricle 212, illustrating the concept of aortic transvalvular pressure gradient as measured by the multi-sensor wire 100 using the method of the first embodiment described above, for a healthy heart and for a heart with stenoses 231, 232 and 233. In this particular example, the aortic transvalvular pressure gradient is the blood pressure measured by sensors at locations P1, P2, P3 and P4 within the left ventricle 212 and the aortic root 210.

The left heart without lesions, illustrated on FIG. 13, would generate aortic and ventricular pressure curves similar to curves 330 and 340, respectively, in FIG. 12. However, the heart illustrated in FIG. 14 has multiple sites of potential blood flow 230 obstructions 231, 232, and 233. In some cases, the operator of the multi-sensor wire 100 might want to measure the blood pressure at several locations, P4 and P3, within the root of the aorta 210 in order to assess a supravalvular aortic stenosis 231 (most commonly an anomalous congenital membrane located in the aortic root).

Figure 15:
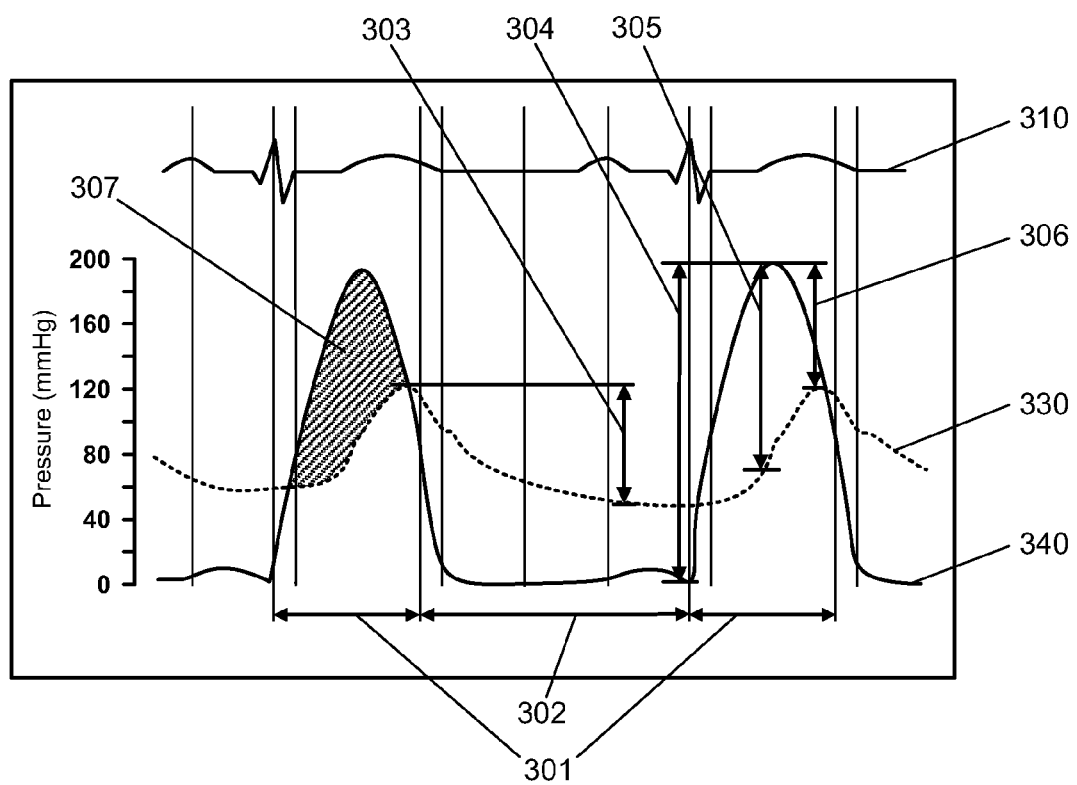
FIG. 15 shows a chart showing typical variations to the blood flow or pressure curves due to cardiac stenosis.

The cardiac hemodynamic data collected from a patient's heart allow a clinician to assess the physiological significance of stenosis lesions. The aortic and ventricular pressure curves from a patient's heart are compared with expected pressure curves. FIG. 15 illustrates typical differences between the aortic 330 and ventricular 340 pressure curves due to intracardiac obstructions. Some of those variations include the maximal difference 305 and the peak-to-peak difference 306 between curves 330 and 340. The area 307 between the aortic pressure curve 330 and ventricle pressure curve 340 is also used to assess the physiological significance of stenosis lesions. The difference between the amplitude 303, 304 of the aortic 330 and ventricle 340 pressure curves is also key information for the clinician.

The medical reference literature relating to cardiac catheterization and hemodynamics provides different possible variations of the aortic 330 and ventricular 340 pressure curves along with the possible causes in order to identify the proper medical diagnosis. For example, cardiac hemodynamic curves, such as shown in FIG. 15, along with analysis of the curves, are provided on pages 647 to 653 of the reference book entitled *Grossman's cardiac catheterization, angiography, and intervention* by Donald S. Bairn and William Grossman.

Figure 16A:
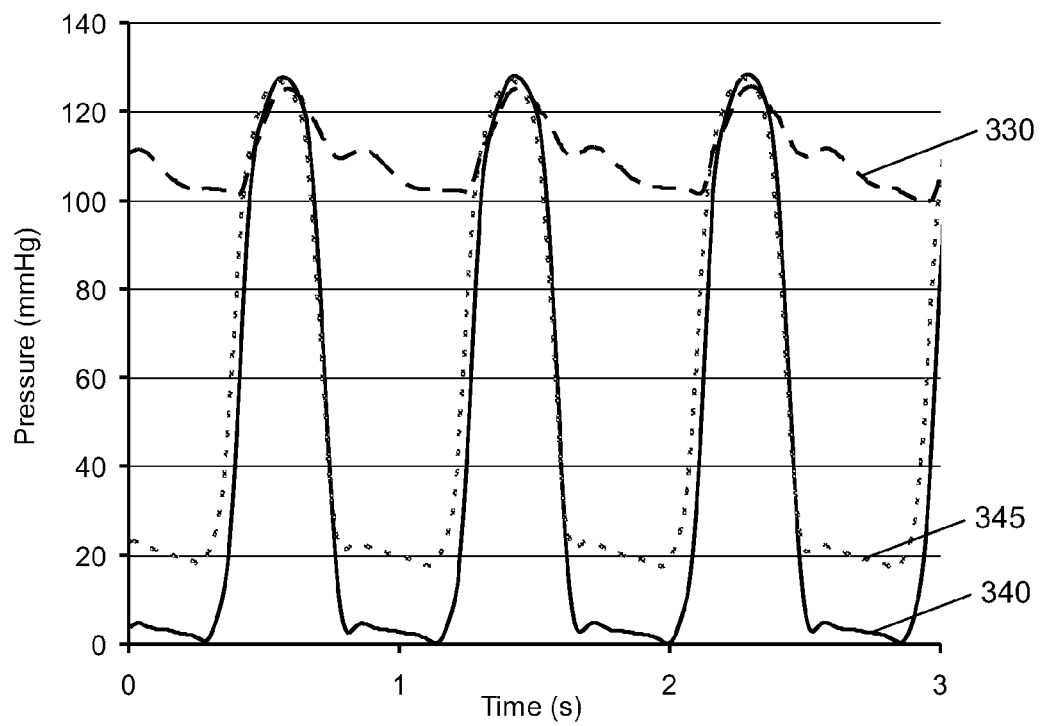
FIGS. 16A and 16B show sample pressure curves, measured over several cycles, across bioprosthetic heart valves, of two different diameters, in a mechanical heart model, using a multi-sensor wire according to the first embodiment.
Figure 16B:
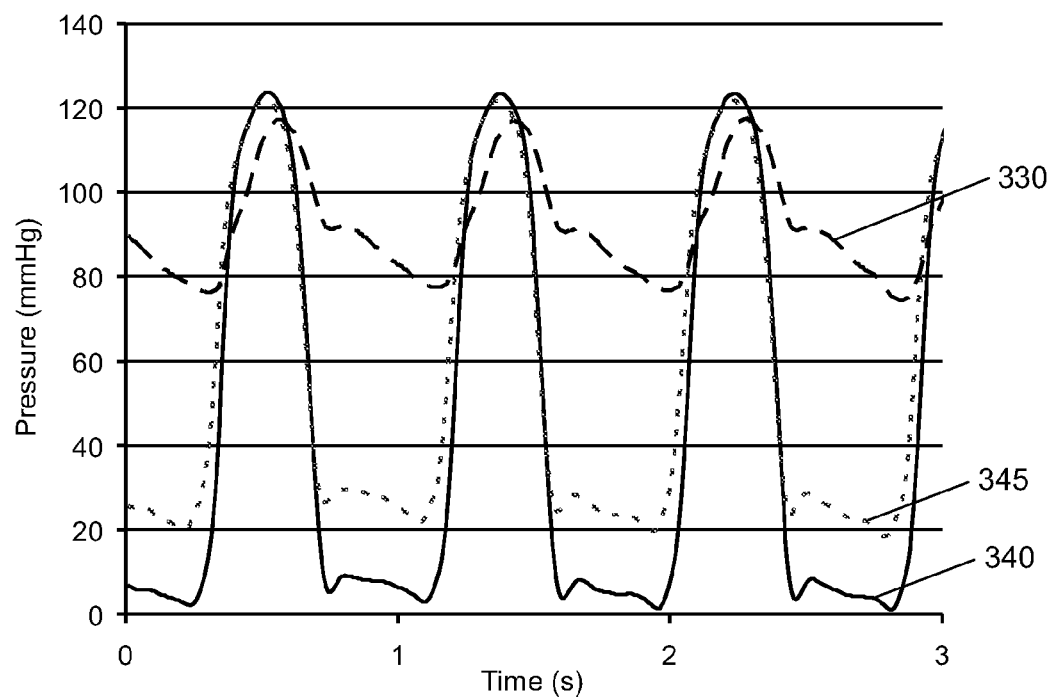

Prototype multi-sensor wires 100 based on the first embodiment, as illustrated schematically in FIG. 1, were assembled and tested. The multi-sensor assembly was fabricated comprising four Fiso FOP-M260 pressure sensors, each sensor 10 being bonded to an individual optical fiber 11, and the multi-sensor assembly was enclosed within a tri-layer polymer tubing of 0.76 mm outside diameter (0.028"), with apertures 12 near each sensor 10. Each sensor has an outside diameter (OD) of 0.260 mm). Each sensor was bonded to an individual 0.125 mm OD optical fiber. The four sensors and their respective optical fibers were assembled to provide a 2 cm spacing between pressure sensors along a length of the distal end of the multi-sensor wire near the distal tip. During the initial in-vitro laboratory testing, the prototypes demonstrated to provide accurate real-time pressure gradient measurements in static water columns. The sensors were calibrated to measure a pressure range from −300 mmHg to 300 mmHg, with an accuracy of ±2 mmHg Subsequently, the prototype multi-sensor wire comprising 4 pressure sensors was tested in a simple activation pulse duplicator system (Vivitro Systems), which is a heart model that simulates cardiac pulse pressures and flows found in the left ventricle and the aorta of a human cardiac system. The duplicator system was equipped with bioprosthetic valves, which were the trileaflet pericardial variety (Perimount 2900 from Carpentier-Edwards). Valves of two different diameters were used in the testing: 29 mm, which simulates a normal healthy valve, and 19 mm, which simulates a valve with reduced aortic valvular area. The multi-sensor wire was inserted through the valve opening such that a pressure sensor P1 was located in the ventricle cavity and another pressure sensor P4 was located in the aortic cavity. FIGS. 16A and 16B show curves 330, 340 representing the pressure readings from pressure sensors P4 (aorta) 330 and P1 (ventricle) 340, for the 29 and 19 mm valves, respectively. A person skilled in the art will observe that the pressure difference between the pressures P1 and P4, for the ventricle and aorta respectively, for the 19 mm diameter valve during the systolic phase is greater than that of the 29 mm valve, and indicates reduced valvular area.

For comparison of the textbook hemodynamic curves shown in FIGS. 12 and 15, with the experimentally measured curves shown in FIGS. 16A and 16B, the corresponding pressure traces have been labeled with the same reference numbers, i.e. in each Figure shows an aortic pressure trace 330 and the ventricular pressure trace 340. In each of the plots shown in FIGS. 16A and 16B, the third curve 345 represents the pressure curve for another sensor P2 located 2 cm from P1 (ventricle). The curve for the other sensor P3 is not shown.

Figure 16C:
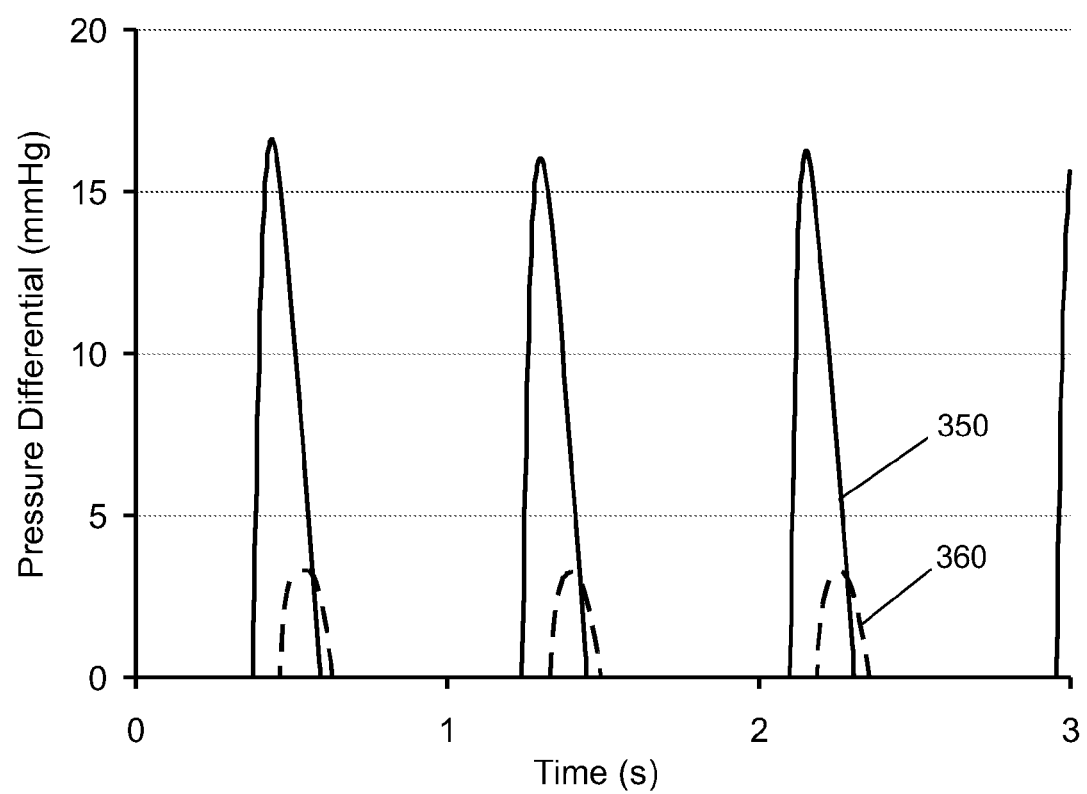
FIG. 16C shows a plot of the positive pressure difference between the ventricular pressure and aortic pressure P1 (ventricle)–P4 (aorta), during several cardiac cycles, for each of the two types of valves tested.

FIG. 16C shows another plot of data from the same experiment. This figure shows the pressure difference P1 (ventricle) minus P4 (aorta) measured by the two pressure sensors located in the ventricle and aorta, respectively, for each of the two valves of different diameter. The differential pressure measurements shown in FIG. 16C emphasize the reduced performance, evidenced by the much larger peak transvalvular pressure difference, for the 19 mm diameter valve (curve 350) relative to the 29 mm valve (curve 360).

It is apparent from these preliminary results that the multi-sensor wire comprising a plurality of optical pressure sensors provides for optical measurement of pressure gradients in an appropriate pressure range and with a suitable sensitivity, accuracy and resolution for measurement of in vivo blood pressure gradients and for obtaining data for aortic and ventricular pressure curves. These initial results demonstrate, prior to in vivo testing and pre-clinical trials, that the multi-sensor wire is effective for measurement of aortic and ventricular pressure curves for assessing operation of bioprosthetic heart valves in a heart model.

In summary, an apparatus, system and methods according to embodiments of the invention are described for simplification of the measurement of a transvalvular pressure gradient for each of the four heart valves. In particular, by using multiple miniaturized sensors, it is possible to measure, simultaneously, the pressure of one part, or the other, of a dysfunctional valve while traversing it with a micro-catheter of diameter 0.89 mm (0.035") or less, comprising a plurality, e.g. four micro pressure sensors. Consequently, one or several sensors can be located on one side or the other of the valve, thus permitting instantaneous measurement, e.g. in the region of maximal obstruction. The small physical size of the device reduces interference with valve operation when it is passes through or is inserted through a valve, e.g. provides less interference with the movement of the valve and/or less perturbation of the transvalvular pressure gradient. Moreover, it enables measurements that permit the determination of whether the stenosis is strictly associated with the valve or not, to a subvalvular stenosis (e.g. sub-aortic hypertrophic stenosis) or supravalvular stenosis. For example, the severity of the aortic stenosis is defined classically by a mean pressure gradient of >50 mmHg or a valvular surface of <0.75 $cm^2$.

In particular, the sensor means may comprise a plurality of pressure sensors, or an array of sensors, in a distal region, or at the distal end, of a guidewire, which is insertable, for example, into a lumen of an artery, or a chamber of the heart. Beneficially the pressure sensor means comprises optical sensors coupled to fine gauge optical fibers that may be introduced into the body with the guidewire, through a catheter. Thus, signals indicative of pressure may be optically detected and eliminate the need for electrical connections to be made along the guidewire, unless other types of electrical sensors are included. Optionally, the apparatus may further comprise temperature sensing means or other sensors of different types. For example, one or more electrical sensors may also be included to allow for measurement of related parameters, e.g. temperature measurements and/or flow measurements measured by resistive sensing means, for example.

For pressure gradient measurements, it will be appreciated that, ideally, data is gathered simultaneously from each of the plurality of pressure sensors, and optionally with simultaneous data from other sensors, e.g. a flow sensor. However, it will be appreciated the system may also be configured to allow for data to be selectively gathered and/or displayed, as needed, from one or more pressure sensor, flow sensor, temperature sensor or other sensors as appropriate, and to allow for data to be graphically displayed over one or more cardiac cycles or other time intervals.

Thus, apparatus according embodiments of the invention provide a medical specialist with a device that permits simultaneous measurements of pressure at several points in the region of interest. Multiple pressure sensors provide for measurement of a pressure gradient in real time. For instance, such a multi-sensor wire or guidewire equipped with a plurality of pressure sensors could evaluate pressure difference upstream and downstream a heart valve. Heart valve degradation could be evaluated based on the measured pressure difference. There are several other examples where simultaneous measurement of pressure at several locations would be advantageous over a single point measurement. For instance such devices could evaluate heart artery blockage, urinary track blockage, thickening of the heart wall (ventricular hypertrophy), for example. Beneficially, the multi-sensor wire enables measurements to be made that allow the cardiac output and valvular area to be determined simultaneously, and more simply and safely compared with existing apparatus and techniques.

The length and diameter of the multi-sensor wire may be selected dependent on the application for which pressure, flow, or temperature is to be measured. For example, cardiovascular applications, such as transvalvular measurements, sensors may be arranged, e.g. equally spaced, along a length of typically 4 cm to 7 cm of the distal end portion of the sensor wire, depending on the size of the heart or region in which measurements are to be made. Other arrangements of the sensors may be desirable depending on the dimensions of the region where measurements are to be made.

In the embodiments described above, the plurality of optical pressure sensors in the multi-sensor assembly are arranged at locations along the distal end portion so that their relative positions are known, i.e. determined by their spacings along the length of the distal end portion. While the distal portion is sufficiently flexible for introduction intravascularly, relative movement of the plurality of sensors is constrained. Thus, when gathering data simultaneously from the sensors, there is greater certainty in the relative location of each of the sensors in the region of interest vs. sequential measurements in different locations using a single sensor guide wire. This is particularly useful for measuring pressures and flows with the heart, where higher flows and turbulence tends to cause excessive movement of single sensors located at the end of a sensor wire. While the embodiments described above focus on measurement and monitoring of transvalvular blood pressure gradients and flow, it will be appreciated that the multi-sensor wire apparatus and methods may be adapted or modified to measure pressure gradients and flow in the blood vessels. When a multi-sensor wire is used for other applications, its outside diameter may have to be reduced to 0.36 mm (0.014") or less. The arrangement of the sensors, e.g. their number, location, and spacing, and the accuracy and pressure measurement range of the pressure sensors may also have to be tailored to meet the specific requirements of the medical application.

Figure 17:
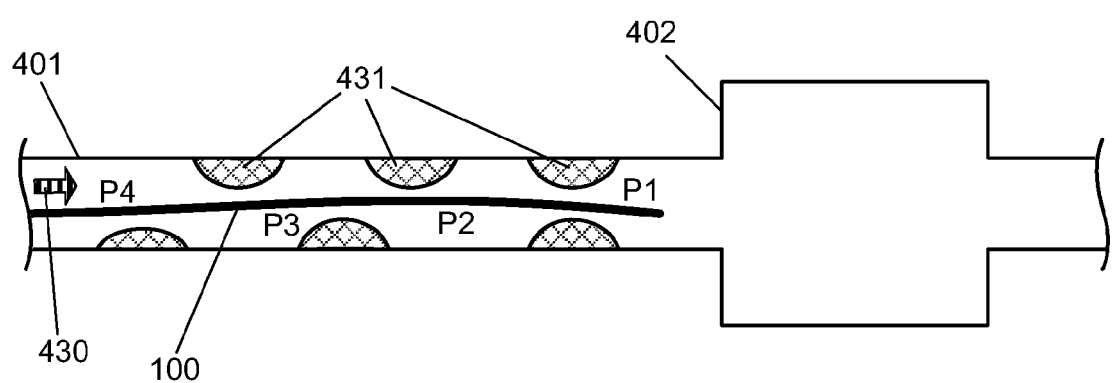
FIG. 17 illustrates schematically positioning of a multi-sensor wire, in the form of micro-catheter or guidewire, within a vessel for pressure measurements by a method according to an embodiment of the invention.

For example, the apparatus may be provided comprising a plurality of optical pressure sensors 10 in the form of a multi-sensor wire 100 that may be introduced into a vessel through a micro-catheter or as a multi-sensor equipped steerable guidewire. Such an apparatus may be configured to measure pressure simultaneously at several locations along a length of a distal portion of the guidewire, as shown schematically in FIG. 17. FIG. 17 shows a simplified schematic of a vessel, such as an artery 401, with multiple stenoses 431, which are restrictions to the blood flow 430. The blood pressure is measured by a multi-sensor wire 100 at four different locations P1, P2, P3 and P4 simultaneously in the vessel.

It will also be appreciated that embodiments of the multi-sensor wire system, apparatus and methods may also have applications for measuring fluid pressures, gradients and flows in other systems of the body, such as the urinary tract, biliary tract or venous system, of animal or human subjects.

In some embodiments all-optical micro-sensors for measurement of both pressure and flow are used to avoid the need for electrical connections altogether, which reduce issues of electromagnetic noise and interference and signal reliability. In other embodiments, optical pressure sensors and one or more electrical sensors, e.g. for flow or temperature, may be combined.

It will be appreciated that in the context of this description, the term "wire" in "multi-sensor wire" or "multi-sensor guidewire" is intended to refer to apparatus having a small diameter and elongated form similar to conventional single sensor wires and guidewires, such as used for cardiac catheterization procedures: i.e. the term "wire" is not intended to be limited to a conventional metallic wire and in a more general sense encompasses an element in the form of a filament, strand, cable or other long, thin (i.e. small diameter) element, so as to conveniently describe the form of a multi-sensor apparatus. As described above, in some embodiments, the multi-sensor wire comprises an assembly of a plurality of optical pressure sensors, which are optically coupled by flexible light guides such as optical fibers, to the optical input/output at proximal end of the apparatus, without electrical components. These components may be integrated with conventional steerable guidewire components. In some embodiments, an electrical sensor with conventional wired electrical connections (i.e. using conventional conductive metallic wires) may be included. In some embodiments, the sensor apparatus may alternatively be referred to as a multi-sensor device, a multi-sensor diagnostic wire or multi-sensor guidewire, for example.

INDUSTRIAL APPLICABILITY

Systems, apparatus and methods according to embodiments of the invention are provided that simplify the measurement of pressure gradients or pressure differences, and/or flow, particularly a transvalvular pressure gradient. Such measurements enable key cardiac parameters to be determined using an improved minimally-invasive procedure. The cardiologist is provided with a tool for more quickly, simply and reliably measuring and monitoring transvalvular pressure gradients, for example, before and after valve repair or replacement procedures.

It will be apparent that the system and apparatus also provide for measurement of pressure gradients for research, testing and assessment of the operation of artificial hearts, prosthetic heart valves, and other synthetic devices for medical use.

In particular, using a multi-sensor device having a diameter of 0.89 mm (0.035") or less, comprising, for example, four pressure sensors and a flow sensor, it is possible for the cardiologist to measure, simultaneously, the pressure at several points from one side to the other of a dysfunctional valve while the sensors of the multi-sensor device are positioned through the valve. For example, if the diameter of the aorta is known, use of a multi-sensor wire capable of simultaneously measuring a pressure gradient and flow, allows for evaluation of the cardiac output and, as a consequence, estimation of, for example, the valve area or lumen area.

One or several sensors can be localized on each side of the valve, permitting instantaneous measurement of a pressure gradient and flow, e.g. in the region of maximal obstruction. Miniaturization of the multi-sensor device, e.g. having a distal portion of 0.46 mm (0.018") diameter or less, means that the presence of the device through the valve has minimal or negligible effect on the movement of the valve and has minimal or negligible repercussions on the measurement of the transvalvular pressure gradient. For example, it permits the cardiologist to make a rapid determination of whether the stenosis is strictly associated with the valve or not, or to a sub-valvular obstruction, e.g. sub-aortic hypertrophic stenosis.

A multi-sensor wire or guidewire, system and methods according to embodiments of the invention may also be used to obtain pressure measurements that can be used to evaluate, in addition to the severity of stenosis of a heart valve, evaluate the severity of stenoses of surrounding regions of the valve, known as subvalvular and supravalvular stenoses. Such evaluation would permit the clinician to determine if valve stenosis is the major impediment to blood flow and warrant a valve repair or replacement.

Although embodiments of the invention have been described and illustrated in detail, it is to be clearly understood that the same is by way of illustration and example only and not to be taken by way of limitation, the scope of the present invention being limited only by the appended claims.

The invention claimed is:

1. An apparatus for measuring an intravascular blood pressure gradient, including a transvalvular blood pressure gradient for a heart valve, comprising:
    a multi-sensor assembly contained within a tubular covering layer;
    the tubular covering layer comprising a micro-catheter or a coil of a steerable guidewire, having a proximal end and a distal end, the distal end comprising a flexible distal tip;
    the multi-sensor assembly comprising:
    an optical fiber bundle comprising a plurality of optical fibers and a plurality of optical sensors, each optical fiber having a proximal end and a distal end,
    each individual one of the plurality of optical sensors being attached and optically coupled to the distal end of a respective individual one of the plurality of optical fibers;
    distal ends of the plurality of optical fibers being arranged to form a sensor arrangement wherein said plurality of optical sensors have sensor locations spaced apart lengthwise from each other;
    the multi-sensor assembly extending within the tubular covering layer from the proximal end into a distal end portion adjacent the distal end;
    the sensor arrangement, comprising said plurality of optical sensors, being located within the distal end portion for measuring pressure at respective sensor locations spaced apart along a length of 4 cm to 7 cm of the distal end portion of the tubular covering layer;
    the proximal end of each one of the plurality of optical fibers being optically coupled to an optical input/output end, for connection to a control system,
    said sensor arrangement providing for a measurement of pressure at each sensor location for determination by the control system of a blood pressure gradient;
    an aperture in the covering layer adjacent each optical sensor for fluid contact;
    at least one marker for locating the sensor arrangement;
    and at least the distal end portion of the covering layer having an outer diameter suitable for introduction intravascularly or intraluminally through a micro-catheter into the heart.

2. The apparatus of claim 1 having a length between the proximal end and the distal end portion in the range from 1 m to 2 m.

3. The apparatus of claim 1, comprising four or more optical pressure sensors arranged at intervals along said length of the distal end portion.

4. The apparatus of claim 1, wherein the micro-catheter of the covering layer comprises a single layer polymer tubing or multilayer polymer tubing.

5. The apparatus of claim 4, wherein the polymer tubing comprises polyimide, polytetrafluorethylene (PTFE), or other suitable bio-compatible or hemo-compatible material.

6. The apparatus of claim 1, wherein each optical sensor extends into a respective adjacent aperture in the tubular covering layer, beyond the inner diameter of the lumen and within the outer diameter of the covering layer.

7. The apparatus of claim 1, wherein the tubular covering layer comprises the coil of a steerable guidewire, further comprising torque steering components for guiding the multi-sensor assembly.

8. The apparatus of claim 1, wherein the tubular covering layer comprises the coil of a steerable guidewire, and further comprising torque steering components including a mandrel extending axially through the length of the multi-sensor assembly from the proximal end to the distal end of the coil, and the guidewire having an external diameter along the length of the distal end portion of 0.89 mm or less and preferably of 0.46 mm or less.

9. The apparatus of claim 1, wherein the flexible distal tip comprises a J-tip.

10. The apparatus of claim 1, wherein said optical input/output of the multi-sensor assembly comprises part of a connector for optically coupling the multi-sensor assembly to the control system.

11. The apparatus of claim 10, wherein the connector further provides electrical connections for an electrical sensor and/or wireless connectivity of the electrical sensor with the control system.

12. The apparatus of claim 1, configured for measuring a transvalvular or intra-arterial blood pressure gradient and flow velocity, wherein:
    the sensor arrangement comprises a plurality of at least four optical pressure sensors and an optical flow sensor arranged along a length of the distal end portion matched to a dimension of the transvalvular or intra-arterial region of interest; and
    each of the sensors and optical fibers having outside diameters such that they are accommodated within a catheter or guidewire having an outside diameter of 0.89 mm or less and preferably of 0.46 mm or less.

13. The apparatus of claim 1, configured for measuring a transvalvular or intra-arterial blood pressure gradient and flow velocity, wherein:
    the sensor arrangement comprises a plurality of at least four optical pressure sensors and an electrical flow sensor arranged along a length of the distal end portion matched to dimensions of the transvalvular or intra-arterial region of interest; and
    each of the optical sensors, the optical fibers, the electrical sensor and electrical connections for the electrical sensor having outside diameters such that they are accommodated within a catheter or guidewire having an outside diameter of 0.89 mm or less and preferably of 0.46 mm or less.

14. A control system for controlling the apparatus of claim 1, wherein the control system comprises a light source and detector for coupling, through h said optical fibers, to each of the optical sensors, and optionally comprises electrical connections for an electrical sensor.

15. The control system of claim 14 wherein the system further comprises a processor configured for processing optical data indicative of pressure gradient values and optionally, optical or electrical data indicative of flow velocity values.

16. The control system of claim 14 for measuring intravascular or transvalvular blood pressure gradients, and further comprising a processor configured for graphically displaying a blood pressure gradient and optionally flow velocity data, for one or more time intervals, and during one or more cardiac cycles.

17. The apparatus of claim 1, wherein said plurality of optical sensors comprise optical pressure sensors spaced at intervals of approximately 2 cm along said length of the distal end portion, for placement of at least one optical pressure sensor upstream and at least one optical pressure sensor downstream of the heart valve.

18. The apparatus of claim 17, wherein said plurality of optical sensors further comprises an optical flow sensor, and wherein the location of the optical flow sensor is proximal to at least some of said optical pressure sensors.

19. The apparatus of claim 1, wherein the covering layer comprises a tubular covering layer having an inner diameter defining a lumen, the multi-sensor assembly extending within the lumen from the proximal end to the distal end portion.

20. The apparatus of claim 1, wherein the optical sensors comprise Micro-Opto-Mechanical Systems (MOMS) pressure sensors.

21. The apparatus of claim 20, wherein the MOMS sensors comprise Fabry-Perot MOMS sensors.

22. The apparatus of claim 1, for measuring a transvalvular blood pressure gradient, wherein the flexible distal tip enables introduction of the distal end portion through a heart valve, and wherein the distal end portion containing the plurality sensors has flexibility to be introduced into a chamber of the heart and through the heart valve, together with stiffness to constrain movement of the plurality of sensors in regions of turbulent flow within the heart.

23. The apparatus of claim 1, wherein the sensor arrangement further comprises an optical sensor for measuring at least one of flow and temperature.

24. The apparatus of claim 23, wherein the optical flow sensor comprises an optical thermoconvection flow sensor.

25. The apparatus of claim 1, wherein the sensor arrangement further comprises an electrical flow sensor and the multi-sensor assembly further comprises electrical connections coupling the electrical flow sensor to an electrical input/output at the proximal end.

26. The apparatus of claim 25, wherein the flow sensor comprises a resistive/ohmic thermoconvection flow sensor or a Doppler effect flow sensor.

27. The apparatus of claim 1, wherein at least the distal end portion of the covering layer has an outer diameter of 0.89 mm or less, and preferably of 0.46 mm or less.

* * * * *